US011844566B2

(12) United States Patent
Fung et al.

(10) Patent No.: US 11,844,566 B2
(45) Date of Patent: *Dec. 19, 2023

(54) DEVICES AND METHODS FOR LEFT ATRIAL APPENDAGE CLOSURE

(71) Applicant: AtriCure, Inc., Mason, OH (US)

(72) Inventors: Gregory W. Fung, Redwood Shores, CA (US); Randall J. Lee, Hillsborough, CA (US); Russell Pong, Newark, CA (US); Robert L. Clark, III, Hayward, CA (US); Arnold M. Escano, San Jose, CA (US)

(73) Assignee: AtriCure, Inc., Mason, OH (US)

( * ) Notice: Subject to any disclaimer, the term of this patent is extended or adjusted under 35 U.S.C. 154(b) by 157 days.

This patent is subject to a terminal disclaimer.

(21) Appl. No.: 17/062,406

(22) Filed: Oct. 2, 2020

(65) Prior Publication Data
US 2021/0205010 A1 Jul. 8, 2021

Related U.S. Application Data

(63) Continuation of application No. 16/289,365, filed on Feb. 28, 2019, now Pat. No. 10,799,288, which is a
(Continued)

(51) Int. Cl.
*A61B 18/00* (2006.01)
*A61B 18/14* (2006.01)
(Continued)

(52) U.S. Cl.
CPC .... *A61B 18/1492* (2013.01); *A61B 17/12013* (2013.01); *A61B 2017/00243* (2013.01);
(Continued)

(58) Field of Classification Search
CPC ................................................. A61B 18/1492
(Continued)

(56) References Cited

U.S. PATENT DOCUMENTS 3,496,932 A 2/1970 Prisk et al.
3,677,597 A 7/1972 Stipek
(Continued)

FOREIGN PATENT DOCUMENTS

CA 2796267 A1 * 10/2011 ....... A61B 17/12013
CN 2624615 Y 7/2004
(Continued)

OTHER PUBLICATIONS afibfacts.com (Date Unknown). "Cox-Maze III: The Gold Standard Treatment for Atrial Fibrillation: Developing a Surgical Option for Atrial Fibrillation," located at <http://www.afibfacts.com/Treatment_Options_for_Atrial_Fibrillation/Cox-Maze_III%_3a_The_Gold_Standard_Treatment_for_Atrial_Fibrillation >, last visited on Apr. 20, 2007, 4 pages.
(Continued)

*Primary Examiner* — Nicole F Lavert
(74) *Attorney, Agent, or Firm* — Levine Bagade Han LLP

(57) ABSTRACT

Described here are devices, systems, and methods for closing the left atrial appendage. The methods described here utilize a closure device for closing the left atrial appendage and guides or expandable elements with ablation or abrading elements to ablate or abrade the left atrial appendage. In general, these methods include positioning a balloon at least partially within the atrial appendage, positioning a closure assembly of a closure device around an exterior of the atrial appendage, inflating the balloon, partially closing the closure assembly, ablating the interior tissue of the atrial appendage with the inflated balloon, removing the balloon from the atrial appendage, and closing the atrial appendage with the closure assembly.

20 Claims, 13 Drawing Sheets

Related U.S. Application Data continuation of application No. 14/530,575, filed on Oct. 31, 2014, now Pat. No. 10,258,408.

(60) Provisional application No. 61/898,382, filed on Oct. 31, 2013.

(51) Int. Cl.
*A61B 17/12* (2006.01)
*A61B 17/00* (2006.01)

(52) U.S. Cl.
CPC .............. *A61B 2017/00477* (2013.01); *A61B 2017/00876* (2013.01); *A61B 2018/0016* (2013.01); *A61B 2018/0022* (2013.01); *A61B 2018/00357* (2013.01); *A61B 2018/00577* (2013.01); *A61B 2018/141* (2013.01); *A61B 2018/142* (2013.01)

(58) Field of Classification Search
USPC .......................................................... 606/41
See application file for complete search history.

(56) References Cited

U.S. PATENT DOCUMENTS

| | | |
|---|---|---|
| 3,802,074 A | 4/1974 | Hoppe |
| 3,841,685 A | 10/1974 | Kolodziej |
| 3,999,555 A | 12/1976 | Person |
| 4,018,229 A | 4/1977 | Komiya |
| 4,030,509 A | 6/1977 | Heilman et al. |
| 4,078,305 A | 3/1978 | Akiyama |
| 4,181,123 A | 1/1980 | Crosby |
| 4,249,536 A | 2/1981 | Vega |
| 4,257,278 A | 3/1981 | Papadofrangakis et al. |
| 4,319,562 A | 3/1982 | Crosby |
| 4,428,375 A | 1/1984 | Ellman |
| 4,596,530 A | 6/1986 | McGlinn |
| 4,662,377 A | 5/1987 | Heilman et al. |
| 4,765,341 A | 8/1988 | Mower et al. |
| 4,817,608 A | 4/1989 | Shapland et al. |
| 4,901,405 A | 2/1990 | Grover et al. |
| 4,944,753 A | 7/1990 | Burgess et al. |
| 4,991,578 A | 2/1991 | Cohen |
| 4,991,603 A | 2/1991 | Cohen et al. |
| 4,998,975 A | 3/1991 | Cohen et al. |
| 5,033,477 A | 7/1991 | Chin et al. |
| 5,108,406 A | 4/1992 | Lee |
| 5,163,942 A | 11/1992 | Rydell |
| 5,163,946 A | 11/1992 | Li |
| 5,176,691 A | 1/1993 | Pierce |
| 5,181,123 A | 1/1993 | Swank |
| 5,181,919 A | 1/1993 | Bergman et al. |
| 5,226,535 A | 7/1993 | Roshdy et al. |
| 5,226,908 A | 7/1993 | Yoon |
| 5,242,459 A | 9/1993 | Buelna |
| 5,243,977 A | 9/1993 | Trabucco et al. |
| 5,269,326 A | 12/1993 | Verrier |
| 5,279,539 A | 1/1994 | Bohan et al. |
| 5,281,238 A | 1/1994 | Chin et al. |
| 5,300,078 A | 4/1994 | Buelna |
| 5,306,234 A | 4/1994 | Johnson |
| 5,318,578 A | 6/1994 | Hasson |
| 5,336,229 A | 8/1994 | Noda |
| 5,336,231 A | 8/1994 | Adair |
| 5,336,252 A | 8/1994 | Cohen |
| 5,385,156 A | 1/1995 | Oliva |
| 5,387,219 A | 2/1995 | Rappe |
| 5,398,944 A | 3/1995 | Holster |
| 5,403,331 A | 4/1995 | Chesterfield et al. |
| 5,405,351 A | 4/1995 | Kinet et al. |
| 5,417,684 A | 5/1995 | Jackson et al. |
| 5,423,821 A | 6/1995 | Pasque |
| 5,423,830 A | 6/1995 | Schneebaum et al. |
| 5,433,457 A | 7/1995 | Wright |
| 5,433,730 A | 7/1995 | Alt |
| 5,443,481 A | 8/1995 | Lee |
| 5,449,361 A | 9/1995 | Preissman |
| 5,449,637 A | 9/1995 | Kadry |
| 5,458,597 A | 10/1995 | Edwards et al. |
| 5,465,731 A | 11/1995 | Bell et al. |
| 5,494,240 A | 2/1996 | Waugh |
| 5,498,228 A | 3/1996 | Royalty et al. |
| 5,522,819 A | 6/1996 | Graves et al. |
| 5,540,711 A | 7/1996 | Kieturakis et al. |
| 5,545,178 A | 8/1996 | Kensey et al. |
| 5,571,161 A | 11/1996 | Starksen |
| 5,591,177 A | 1/1997 | Lehrer |
| 5,609,597 A | 3/1997 | Lehrer |
| 5,624,430 A | 4/1997 | Eton et al. |
| 5,624,453 A | 4/1997 | Ahmed |
| 5,634,895 A | 6/1997 | Igo et al. |
| 5,636,780 A | 6/1997 | Green et al. |
| 5,676,162 A | 10/1997 | Larson, Jr. et al. |
| 5,676,651 A | 10/1997 | Larson, Jr. et al. |
| 5,678,547 A | 10/1997 | Faupel et al. |
| 5,681,278 A | 10/1997 | Igo et al. |
| 5,682,906 A | 11/1997 | Sterman et al. |
| 5,683,348 A | 11/1997 | Diener |
| 5,683,364 A | 11/1997 | Zadini et al. |
| 5,683,445 A | 11/1997 | Swoyer |
| 5,693,059 A | 12/1997 | Yoon |
| 5,693,091 A | 12/1997 | Larson, Jr. et al. |
| 5,699,748 A | 12/1997 | Linskey, Jr. et al. |
| 5,702,430 A | 12/1997 | Larson, Jr. et al. |
| 5,707,336 A | 1/1998 | Rubin |
| 5,716,367 A | 2/1998 | Koike et al. |
| 5,716,392 A | 2/1998 | Bourgeois et al. |
| 5,727,569 A | 3/1998 | Benetti et al. |
| 5,728,151 A | 3/1998 | Garrison et al. |
| 5,735,877 A | 4/1998 | Pagedas |
| 5,741,281 A | 4/1998 | Martin |
| 5,752,526 A | 5/1998 | Cosgrove |
| 5,766,151 A | 6/1998 | Valley et al. |
| 5,766,216 A | 6/1998 | Gangal et al. |
| 5,766,217 A | 6/1998 | Christy |
| 5,769,863 A | 6/1998 | Garrison |
| 5,779,727 A | 7/1998 | Orejola |
| 5,788,715 A | 8/1998 | Watson, Jr. et al. |
| 5,792,151 A | 8/1998 | Heck et al. |
| 5,797,870 A | 8/1998 | March et al. |
| 5,797,929 A | 8/1998 | Andreas et al. |
| 5,797,946 A | 8/1998 | Chin |
| 5,799,661 A | 9/1998 | Boyd et al. |
| 5,810,845 A | 9/1998 | Yoon |
| 5,814,052 A | 9/1998 | Nakao et al. |
| 5,823,946 A | 10/1998 | Chin |
| 5,827,216 A | 10/1998 | Igo et al. |
| 5,840,059 A | 11/1998 | March et al. |
| 5,855,586 A | 1/1999 | Habara et al. |
| 5,865,791 A | 2/1999 | Whayne et al. |
| 5,871,531 A | 2/1999 | Struble |
| 5,873,876 A | 2/1999 | Christy |
| 5,879,375 A | 3/1999 | Larson, Jr. et al. |
| 5,882,299 A | 3/1999 | Rastegar et al. |
| 5,893,869 A | 4/1999 | Barnhart et al. |
| 5,895,298 A | 4/1999 | Faupel et al. |
| 5,895,404 A | 4/1999 | Ruiz |
| 5,897,586 A | 4/1999 | Molina |
| 5,900,433 A | 5/1999 | Igo et al. |
| 5,906,579 A | 5/1999 | Vander Salm et al. |
| 5,906,620 A | 5/1999 | Nakao et al. |
| 5,908,429 A | 6/1999 | Yoon |
| 5,908,435 A | 6/1999 | Samuels |
| 5,910,124 A | 6/1999 | Rubin |
| 5,910,129 A | 6/1999 | Koblish et al. |
| 5,921,994 A | 7/1999 | Andreas et al. |
| 5,924,424 A | 7/1999 | Stevens et al. |
| RE36,269 E | 8/1999 | Wright |
| 5,941,819 A | 8/1999 | Chin |
| 5,957,936 A | 9/1999 | Yoon et al. |
| 5,961,440 A | 10/1999 | Schweich, Jr. et al. |
| 5,964,699 A | 10/1999 | Rullo et al. |
| 5,968,010 A | 10/1999 | Waxman et al. |

(56) References Cited

U.S. PATENT DOCUMENTS

| | | |
|---|---|---|
| 5,972,013 A | 10/1999 | Schmidt |
| 5,984,866 A | 11/1999 | Rullo et al. |
| 5,984,917 A | 11/1999 | Fleischman et al. |
| 5,991,668 A | 11/1999 | Leinders et al. |
| 5,997,525 A | 12/1999 | March et al. |
| 6,006,122 A | 12/1999 | Smits |
| 6,010,531 A | 1/2000 | Donlon et al. |
| 6,015,382 A | 1/2000 | Zwart et al. |
| 6,027,499 A | 2/2000 | Johnston et al. |
| 6,045,570 A | 4/2000 | Epstein et al. |
| 6,048,329 A | 4/2000 | Thompson et al. |
| 6,059,750 A | 5/2000 | Fogarty et al. |
| 6,067,942 A | 5/2000 | Fernandez |
| 6,071,281 A | 6/2000 | Burnside et al. |
| 6,081,738 A | 6/2000 | Hinohara et al. |
| 6,083,153 A | 7/2000 | Rullo et al. |
| 6,090,042 A | 7/2000 | Rullo et al. |
| 6,095,968 A | 8/2000 | Snyders |
| 6,110,170 A | 8/2000 | Taylor et al. |
| 6,120,431 A | 9/2000 | Magovern et al. |
| 6,132,438 A | 10/2000 | Fleischman et al. |
| 6,148,230 A | 11/2000 | KenKnight |
| 6,149,595 A | 11/2000 | Seitz et al. |
| 6,152,144 A | 11/2000 | Lesh et al. |
| 6,152,920 A | 11/2000 | Thompson et al. |
| 6,152,936 A | 11/2000 | Christy et al. |
| 6,155,968 A | 12/2000 | Wilk |
| 6,157,852 A | 12/2000 | Selmon et al. |
| 6,161,543 A | 12/2000 | Cox et al. |
| 6,162,195 A | 12/2000 | Igo et al. |
| 6,167,889 B1 | 1/2001 | Benetti |
| 6,199,556 B1 | 3/2001 | Benetti et al. |
| 6,200,303 B1 | 3/2001 | Verrior et al. |
| 6,206,004 B1 | 3/2001 | Schmidt et al. |
| 6,224,584 B1 | 5/2001 | March et al. |
| 6,231,518 B1 | 5/2001 | Grabek et al. |
| 6,237,605 B1 | 5/2001 | Vaska et al. |
| 6,241,667 B1 | 6/2001 | Vetter et al. |
| 6,258,021 B1 | 7/2001 | Wilk |
| 6,266,550 B1 | 7/2001 | Selmon et al. |
| 6,280,415 B1 | 8/2001 | Johnson |
| 6,283,127 B1 | 9/2001 | Sterman et al. |
| 6,290,674 B1 | 9/2001 | Roue et al. |
| 6,293,906 B1 | 9/2001 | Vanden Hoek et al. |
| 6,296,630 B1 | 10/2001 | Altman et al. |
| 6,311,692 B1 | 11/2001 | Vaska et al. |
| 6,311,693 B1 | 11/2001 | Sterman et al. |
| 6,314,962 B1 | 11/2001 | Vaska et al. |
| 6,314,963 B1 | 11/2001 | Vaska et al. |
| 6,319,201 B1 | 11/2001 | Wilk |
| 6,333,347 B1 | 12/2001 | Hunter et al. |
| 6,346,074 B1 | 2/2002 | Roth |
| 6,379,366 B1 | 4/2002 | Fleischman et al. |
| 6,423,051 B1 | 7/2002 | Kaplan et al. |
| 6,474,340 B1 | 11/2002 | Vaska et al. |
| 6,485,407 B2 | 11/2002 | Alferness et al. |
| 6,488,689 B1 | 12/2002 | Kaplan et al. |
| 6,494,211 B1 | 12/2002 | Boyd et al. |
| 6,551,303 B1 | 4/2003 | Van Tassel et al. |
| 6,561,969 B2 | 5/2003 | Frazier et al. |
| 6,592,552 B1 | 7/2003 | Schmidt |
| 6,610,055 B1 | 8/2003 | Swanson et al. |
| 6,610,072 B1 | 8/2003 | Christy et al. |
| 6,613,062 B1 | 9/2003 | Leckrone et al. |
| 6,632,229 B1 | 10/2003 | Yamanouchi |
| 6,652,555 B1 | 11/2003 | VanTassel et al. |
| 6,656,175 B2 | 12/2003 | Francischelli et al. |
| 6,666,861 B2 | 12/2003 | Grabek |
| 6,692,491 B1 | 2/2004 | Phan |
| 6,733,509 B2 | 5/2004 | Nobles et al. |
| 6,736,774 B2 | 5/2004 | Benetti et al. |
| 6,755,338 B2 | 6/2004 | Hahnen et al. |
| 6,786,898 B2 | 9/2004 | Guenst |
| 6,789,509 B1 | 9/2004 | Motsinger |
| 6,830,174 B2 | 12/2004 | Hillstead et al. |
| 6,830,576 B2 | 12/2004 | Fleischman et al. |
| 6,840,246 B2 | 1/2005 | Downing |
| 6,985,776 B2 | 1/2006 | Kane et al. |
| 7,011,671 B2 | 3/2006 | Welch |
| 7,041,111 B2 | 5/2006 | Chu |
| 7,056,294 B2 | 6/2006 | Khairkhahan et al. |
| 7,063,682 B1 | 6/2006 | Whayne et al. |
| 7,063,693 B2 | 6/2006 | Guenst |
| 7,175,619 B2 | 2/2007 | Koblish et al. |
| 7,186,214 B2 | 3/2007 | Ness |
| 7,207,988 B2 | 4/2007 | Leckrone et al. |
| 7,226,440 B2 | 6/2007 | Gelfand et al. |
| 7,226,458 B2 | 6/2007 | Kaplan et al. |
| 7,264,587 B2 | 9/2007 | Chin |
| 7,294,115 B1 | 11/2007 | Wilk |
| 7,297,144 B2 | 11/2007 | Fleischman et al. |
| 7,309,328 B2 | 12/2007 | Kaplan et al. |
| 7,318,829 B2 | 1/2008 | Kaplan et al. |
| 7,326,221 B2 | 2/2008 | Sakamoto et al. |
| 7,331,979 B2 | 2/2008 | Khosravi et al. |
| 7,473,260 B2 | 1/2009 | Opolski et al. |
| 7,597,705 B2 | 10/2009 | Forsberg et al. |
| 7,608,091 B2 | 10/2009 | Goldfarb et al. |
| 7,610,104 B2 | 10/2009 | Kaplan et al. |
| 7,618,425 B2 | 11/2009 | Yamamoto et al. |
| 7,681,579 B2 | 3/2010 | Schwartz |
| 7,722,641 B2 | 5/2010 | van der Burg et al. |
| 7,736,347 B2 | 6/2010 | Kaplan et al. |
| 7,828,810 B2 | 11/2010 | Liddicoat et al. |
| 7,846,168 B2 | 12/2010 | Liddicoat et al. |
| 7,905,900 B2 | 3/2011 | Palermo et al. |
| 7,918,865 B2 | 4/2011 | Liddicoat et al. |
| 8,070,693 B2 | 12/2011 | Ayala et al. |
| 8,105,342 B2 | 1/2012 | Onuki et al. |
| 8,157,818 B2 | 4/2012 | Gartner et al. |
| 8,287,561 B2 | 10/2012 | Nunez et al. |
| 8,469,983 B2 | 6/2013 | Fung et al. |
| 8,500,768 B2 | 8/2013 | Cohen |
| 8,636,767 B2 | 1/2014 | McClain |
| 8,715,302 B2 | 5/2014 | Ibrahim et al. |
| 8,721,663 B2 | 5/2014 | Kaplan et al. |
| 8,771,297 B2 | 7/2014 | Miller et al. |
| 8,795,297 B2 | 8/2014 | Liddicoat et al. |
| 8,795,310 B2 | 8/2014 | Fung et al. |
| 8,814,778 B2 | 8/2014 | Kiser et al. |
| 8,932,276 B1 | 1/2015 | Morriss et al. |
| 8,961,543 B2 | 2/2015 | Friedman et al. |
| 8,974,473 B2 | 3/2015 | Kaplan et al. |
| 8,986,278 B2 | 3/2015 | Fung et al. |
| 8,986,325 B2 | 3/2015 | Miller et al. |
| 8,996,133 B2 | 3/2015 | Kaplan et al. |
| 9,089,324 B2 | 7/2015 | McCaw et al. |
| 9,186,174 B2 | 11/2015 | Krishnan et al. |
| 9,198,664 B2 | 12/2015 | Fung et al. |
| 9,198,683 B2 | 12/2015 | Friedman et al. |
| 9,271,819 B2 | 3/2016 | Liddicoat et al. |
| 9,339,295 B2 | 5/2016 | Fung et al. |
| 9,408,608 B2 | 8/2016 | Clark, III et al. |
| 9,486,281 B2 | 11/2016 | Fung et al. |
| 9,498,206 B2 | 11/2016 | Fung et al. |
| 9,498,223 B2 | 11/2016 | Miller et al. |
| 9,522,006 B2 | 12/2016 | Liddicoat et al. |
| 9,724,105 B2 | 8/2017 | Kaplan et al. |
| 9,877,780 B2 | 1/2018 | Longoria |
| 9,936,956 B2 | 4/2018 | Fung et al. |
| 9,956,036 B2 | 5/2018 | Whayne et al. |
| 10,130,369 B2 | 11/2018 | Fung et al. |
| 10,136,909 B2 | 11/2018 | Ibrahim et al. |
| 10,251,650 B2 | 4/2019 | Clark et al. |
| 10,258,408 B2 | 4/2019 | Fung et al. |
| 10,292,710 B2 | 5/2019 | Clark et al. |
| 10,327,780 B2 | 6/2019 | Liddicoat et al. |
| 10,405,919 B2 | 9/2019 | Fung et al. |
| 10,799,288 B2 | 10/2020 | Fung et al. |
| 10,806,460 B2 | 10/2020 | Liddicoat et al. |
| 10,959,734 B2 | 3/2021 | Fung et al. |
| 10,959,752 B2 | 3/2021 | Fung et al. |
| 2001/0003795 A1 | 6/2001 | Suresh et al. |
| 2001/0007070 A1 | 7/2001 | Stewart et al. |

(56) References Cited

U.S. PATENT DOCUMENTS

| | | |
|---|---|---|
| 2001/0025132 A1 | 9/2001 | Alferness et al. |
| 2002/0002329 A1 | 1/2002 | Avitall |
| 2002/0017306 A1 | 2/2002 | Cox et al. |
| 2002/0022860 A1 | 2/2002 | Borillo et al. |
| 2002/0032440 A1 | 3/2002 | Hooven et al. |
| 2002/0045895 A1 | 4/2002 | Sliwa, Jr. et al. |
| 2002/0049457 A1 | 4/2002 | Kaplan et al. |
| 2002/0058925 A1 | 5/2002 | Kaplan et al. |
| 2002/0062136 A1 | 5/2002 | Hillstead et al. |
| 2002/0068970 A1 | 6/2002 | Cox et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111636 A1 | 8/2002 | Fleischman et al. |
| 2002/0111637 A1 | 8/2002 | Kaplan et al. |
| 2002/0123771 A1 | 9/2002 | Ideker et al. |
| 2002/0128639 A1 | 9/2002 | Pless et al. |
| 2002/0143326 A1* | 10/2002 | Foley ............ A61B 18/1492 606/41 |
| 2002/0147456 A1 | 10/2002 | Diduch et al. |
| 2003/0014049 A1 | 1/2003 | Koblish et al. |
| 2003/0024537 A1 | 2/2003 | Cox et al. |
| 2003/0045900 A1 | 3/2003 | Hahnen et al. |
| 2003/0069577 A1 | 4/2003 | Vaska et al. |
| 2003/0078465 A1 | 4/2003 | Pai et al. |
| 2003/0083542 A1 | 5/2003 | Alferness et al. |
| 2003/0083674 A1 | 5/2003 | Gibbens, III |
| 2003/0109863 A1 | 6/2003 | Francischelli et al. |
| 2003/0120264 A1 | 6/2003 | Lattouf |
| 2003/0120337 A1 | 6/2003 | Van Tassel et al. |
| 2003/0158464 A1 | 8/2003 | Bertolero |
| 2003/0181942 A1 | 9/2003 | Sutton et al. |
| 2003/0187460 A1 | 10/2003 | Chin et al. |
| 2003/0220667 A1 | 11/2003 | Van der Burg et al. |
| 2003/0236535 A1 | 12/2003 | Onuki et al. |
| 2004/0024414 A1 | 2/2004 | Downing |
| 2004/0030335 A1 | 2/2004 | Zenati et al. |
| 2004/0034347 A1 | 2/2004 | Hall et al. |
| 2004/0044361 A1 | 3/2004 | Frazier et al. |
| 2004/0049210 A1 | 3/2004 | VanTassel et al. |
| 2004/0059280 A1 | 3/2004 | Makower et al. |
| 2004/0059352 A1 | 3/2004 | Burbank et al. |
| 2004/0064138 A1 | 4/2004 | Grabek |
| 2004/0068267 A1 | 4/2004 | Harvie et al. |
| 2004/0078069 A1 | 4/2004 | Francischelli et al. |
| 2004/0102804 A1 | 5/2004 | Chin |
| 2004/0106918 A1 | 6/2004 | Cox et al. |
| 2004/0111101 A1 | 6/2004 | Chin |
| 2004/0116943 A1 | 6/2004 | Brandt et al. |
| 2004/0122467 A1 | 6/2004 | Van Tassel et al. |
| 2004/0148020 A1 | 7/2004 | Vidlund et al. |
| 2004/0158127 A1 | 8/2004 | Okada |
| 2004/0162579 A1 | 8/2004 | Foerster |
| 2004/0225212 A1 | 11/2004 | Okerlund et al. |
| 2004/0225300 A1 | 11/2004 | Goldfarb et al. |
| 2004/0243176 A1 | 12/2004 | Hahnen et al. |
| 2004/0260273 A1 | 12/2004 | Wan |
| 2005/0033274 A1 | 2/2005 | Pless et al. |
| 2005/0033280 A1 | 2/2005 | Francischelli et al. |
| 2005/0033287 A1 | 2/2005 | Sra |
| 2005/0033321 A1 | 2/2005 | Fleischman et al. |
| 2005/0043743 A1 | 2/2005 | Dennis |
| 2005/0043745 A1 | 2/2005 | Alferness et al. |
| 2005/0080454 A1 | 4/2005 | Drews et al. |
| 2005/0085843 A1 | 4/2005 | Opolski et al. |
| 2005/0101984 A1 | 5/2005 | Chanduszko et al. |
| 2005/0107824 A1 | 5/2005 | Hillstead et al. |
| 2005/0113861 A1 | 5/2005 | Corcoran et al. |
| 2005/0149068 A1 | 7/2005 | Williams et al. |
| 2005/0149069 A1 | 7/2005 | Bertolero et al. |
| 2005/0154376 A1 | 7/2005 | Riviere et al. |
| 2005/0165466 A1 | 7/2005 | Morris et al. |
| 2005/0187545 A1 | 8/2005 | Hooven et al. |
| 2005/0228422 A1 | 10/2005 | Machold et al. |
| 2005/0256532 A1 | 11/2005 | Nayak et al. |
| 2006/0004323 A1 | 1/2006 | Chang et al. |
| 2006/0004388 A1 | 1/2006 | Whayne et al. |
| 2006/0009715 A1 | 1/2006 | Khairkhahan et al. |
| 2006/0009756 A1 | 1/2006 | Francischelli et al. |
| 2006/0020162 A1 | 1/2006 | Whayne et al. |
| 2006/0020271 A1 | 1/2006 | Stewart et al. |
| 2006/0020336 A1 | 1/2006 | Liddicoat |
| 2006/0034930 A1 | 2/2006 | Khosravi et al. |
| 2006/0095066 A1 | 5/2006 | Chang et al. |
| 2006/0100545 A1 | 5/2006 | Ayala et al. |
| 2006/0106278 A1 | 5/2006 | Machold et al. |
| 2006/0200120 A1 | 9/2006 | DiCarlo et al. |
| 2006/0200169 A1 | 9/2006 | Sniffin |
| 2006/0212045 A1 | 9/2006 | Schilling et al. |
| 2006/0247672 A1 | 11/2006 | Vidlund et al. |
| 2006/0253128 A1 | 11/2006 | Sekine et al. |
| 2006/0253129 A1 | 11/2006 | Liddicoat et al. |
| 2007/0010829 A1 | 1/2007 | Nobles et al. |
| 2007/0016228 A1 | 1/2007 | Salas |
| 2007/0027456 A1 | 2/2007 | Gartner et al. |
| 2007/0038229 A1 | 2/2007 | de la Torre |
| 2007/0043344 A1 | 2/2007 | McAuley |
| 2007/0060951 A1 | 3/2007 | Shannon |
| 2007/0083082 A1 | 4/2007 | Kiser et al. |
| 2007/0083194 A1 | 4/2007 | Kunis et al. |
| 2007/0083225 A1 | 4/2007 | Kiser et al. |
| 2007/0083230 A1 | 4/2007 | Javois |
| 2007/0083232 A1 | 4/2007 | Lee |
| 2007/0088369 A1 | 4/2007 | Shaw et al. |
| 2007/0100405 A1 | 5/2007 | Thompson et al. |
| 2007/0135822 A1 | 6/2007 | Onuki et al. |
| 2007/0149988 A1 | 6/2007 | Michler et al. |
| 2007/0156217 A1 | 7/2007 | Kaplan et al. |
| 2007/0156220 A1 | 7/2007 | Kaplan et al. |
| 2007/0179345 A1 | 8/2007 | Santilli |
| 2007/0219546 A1 | 9/2007 | Mody et al. |
| 2007/0249991 A1 | 10/2007 | Whayne et al. |
| 2007/0260278 A1 | 11/2007 | Wheeler et al. |
| 2007/0270637 A1 | 11/2007 | Takemoto et al. |
| 2007/0270891 A1 | 11/2007 | McGuckin, Jr. |
| 2007/0299496 A1 | 12/2007 | Podmore et al. |
| 2008/0009843 A1 | 1/2008 | de la Torre |
| 2008/0015406 A1 | 1/2008 | Dlugos et al. |
| 2008/0015571 A1 | 1/2008 | Rubinsky et al. |
| 2008/0033241 A1 | 2/2008 | Peh et al. |
| 2008/0033457 A1 | 2/2008 | Francischelli et al. |
| 2008/0039879 A1 | 2/2008 | Chin et al. |
| 2008/0058635 A1 | 3/2008 | Halperin et al. |
| 2008/0097489 A1 | 4/2008 | Goldfarb et al. |
| 2008/0154260 A1 | 6/2008 | Hoof |
| 2008/0177381 A1 | 7/2008 | Navia et al. |
| 2008/0214889 A1 | 9/2008 | Saadat et al. |
| 2008/0228265 A1 | 9/2008 | Spence et al. |
| 2008/0243183 A1 | 10/2008 | Miller et al. |
| 2008/0245371 A1 | 10/2008 | Gruber |
| 2008/0269782 A1 | 10/2008 | Stefanchik et al. |
| 2008/0294174 A1 | 11/2008 | Bardsley et al. |
| 2008/0294175 A1 | 11/2008 | Bardsley et al. |
| 2008/0312664 A1 | 12/2008 | Bardsley et al. |
| 2009/0043317 A1 | 2/2009 | Cavanaugh et al. |
| 2009/0088728 A1 | 4/2009 | Dollar et al. |
| 2009/0088778 A1 | 4/2009 | Miyamoto et al. |
| 2009/0093809 A1 | 4/2009 | Anderson et al. |
| 2009/0124847 A1 | 5/2009 | Doty et al. |
| 2009/0182326 A1 | 7/2009 | Zenati et al. |
| 2009/0196696 A1 | 8/2009 | Otsuka et al. |
| 2009/0287203 A1 | 11/2009 | Mazzone et al. |
| 2010/0069925 A1 | 3/2010 | Friedman et al. |
| 2010/0094314 A1 | 4/2010 | Hernlund |
| 2010/0174296 A1 | 7/2010 | Vakharia et al. |
| 2010/0191253 A1 | 7/2010 | Oostman et al. |
| 2010/0286718 A1 | 11/2010 | Kassab et al. |
| 2010/0331820 A1 | 12/2010 | Giuseppe et al. |
| 2011/0034804 A1 | 2/2011 | Hubregtse et al. |
| 2011/0060350 A1 | 3/2011 | Powers et al. |
| 2011/0082495 A1 | 4/2011 | Ruiz |
| 2011/0087270 A1 | 4/2011 | Penner et al. |
| 2011/0092997 A1 | 4/2011 | Kang |
| 2011/0106107 A1 | 5/2011 | Binmoeller et al. |

(56) References Cited

U.S. PATENT DOCUMENTS

| | | |
|---|---|---|
| 2011/0112537 A1 | 5/2011 | Bernstein et al. |
| 2011/0282250 A1 | 11/2011 | Fung et al. |
| 2011/0295060 A1 | 12/2011 | Zenati et al. |
| 2012/0022558 A1 | 1/2012 | Friedman et al. |
| 2012/0029512 A1 | 2/2012 | Willard et al. |
| 2012/0143177 A1 | 6/2012 | Avitall et al. |
| 2012/0158022 A1 | 6/2012 | Kaplan et al. |
| 2012/0209300 A1 | 8/2012 | Torrie |
| 2012/0330351 A1 | 12/2012 | Friedman et al. |
| 2013/0144311 A1* | 6/2013 | Fung ............ A61B 17/12013 606/139 |
| 2013/0218156 A1 | 8/2013 | Kassab et al. |
| 2013/0296880 A1 | 11/2013 | Kelley et al. |
| 2014/0018831 A1 | 1/2014 | Kassab et al. |
| 2014/0171733 A1 | 6/2014 | Sternik |
| 2014/0222138 A1 | 8/2014 | Machold et al. |
| 2014/0276911 A1 | 9/2014 | Smith et al. |
| 2014/0316385 A1 | 10/2014 | Longoria et al. |
| 2014/0330074 A1 | 11/2014 | Morriss et al. |
| 2014/0336572 A1 | 11/2014 | Heisel et al. |
| 2014/0336676 A1 | 11/2014 | Pong et al. |
| 2014/0364901 A1 | 12/2014 | Kiser et al. |
| 2014/0364907 A1 | 12/2014 | White et al. |
| 2014/0371741 A1 | 12/2014 | Longoria et al. |
| 2015/0018853 A1 | 1/2015 | Friedman et al. |
| 2015/0025312 A1 | 1/2015 | de Canniere |
| 2015/0173765 A1 | 1/2015 | Friedman et al. |
| 2015/0157328 A1 | 6/2015 | Miller et al. |
| 2015/0182225 A1 | 7/2015 | Morejohn et al. |
| 2015/0190135 A1 | 7/2015 | Ibrahim et al. |
| 2015/0223813 A1 | 8/2015 | Willisamson et al. |
| 2015/0250482 A1 | 9/2015 | Slaughter et al. |
| 2015/0374380 A1 | 12/2015 | Miller et al. |
| 2016/0008001 A1 | 1/2016 | Winkler et al. |
| 2016/0008061 A1* | 1/2016 | Fung ............ A61B 18/1815 606/1 |
| 2016/0066974 A1 | 3/2016 | Coulombe |
| 2016/0106421 A1 | 4/2016 | Eliachar et al. |
| 2016/0120549 A1 | 5/2016 | Fung et al. |
| 2016/0278781 A1 | 9/2016 | Fung et al. |
| 2016/0310144 A1 | 10/2016 | Kimura et al. |
| 2016/0310145 A1 | 10/2016 | Clark et al. |
| 2016/0317155 A1 | 11/2016 | Kimura et al. |
| 2016/0346028 A1 | 12/2016 | Rogers et al. |
| 2017/0209141 A1 | 7/2017 | Fung et al. |
| 2017/0290592 A1 | 10/2017 | Miller et al. |
| 2017/0325819 A1 | 11/2017 | Kaplan et al. |
| 2018/0008342 A1 | 1/2018 | Ibrahim et al. |
| 2018/0085130 A1 | 3/2018 | Fung et al. |
| 2018/0310941 A1 | 11/2018 | Fung et al. |
| 2019/0274690 A1 | 9/2019 | Clark et al. |
| 2019/0290285 A1 | 9/2019 | Liddicoat et al. |
| 2019/0298376 A1 | 10/2019 | Clark et al. |

FOREIGN PATENT DOCUMENTS

| | | |
|---|---|---|
| CN | 101242785 A | 8/2008 |
| CN | 101262823 B | 12/2011 |
| EP | 0 598 219 A2 | 5/1994 |
| EP | 0 598 219 A3 | 5/1994 |
| EP | 0 598 219 B1 | 5/1994 |
| EP | 0 625 336 A2 | 11/1994 |
| EP | 0 705 566 A1 | 4/1996 |
| EP | 1 010 397 A1 | 6/2000 |
| GB | 1 506 142 A | 4/1978 |
| JP | H-6-319742 A | 11/1994 |
| JP | 7-296645 A2 | 11/1995 |
| JP | 7-299073 A | 11/1995 |
| JP | 11-507262 A | 6/1999 |
| JP | 2001-120560 A | 5/2001 |
| JP | 2002-512071 A | 4/2002 |
| JP | 2002-540834 A | 12/2002 |
| JP | 2002-540901 A | 12/2002 |
| JP | 2003-225241 A | 8/2003 |
| JP | 2004-000601 A | 1/2004 |
| JP | 2005-110860 A | 4/2005 |
| JP | 2005-296645 A | 10/2005 |
| JP | 2005-531360 A | 10/2005 |
| JP | 2007-504886 A | 3/2007 |
| JP | 2007-534355 A | 11/2007 |
| JP | 2008-534085 A | 8/2008 |
| JP | 2010-523171 A | 7/2010 |
| JP | 2012-522596 A | 9/2012 |
| WO | WO-94/01045 A1 | 1/1994 |
| WO | WO-94/04079 A1 | 3/1994 |
| WO | WO-94/08514 A1 | 4/1994 |
| WO | WO-96/04854 A1 | 2/1996 |
| WO | WO-96/40356 A1 | 12/1996 |
| WO | WO-97/11644 A1 | 4/1997 |
| WO | WO-97/43957 A1 | 11/1997 |
| WO | WO-99/53845 A1 | 10/1999 |
| WO | WO-00/59383 A1 | 10/2000 |
| WO | WO-00/61202 A1 | 10/2000 |
| WO | WO-03/028558 A2 | 4/2003 |
| WO | WO-03/028558 A3 | 4/2003 |
| WO | WO-2004/002327 A1 | 1/2004 |
| WO | WO-2004/066828 A2 | 8/2004 |
| WO | WO-2004/066828 A3 | 8/2004 |
| WO | WO-2005/034767 A1 | 4/2005 |
| WO | WO-2005/034802 A2 | 4/2005 |
| WO | WO-2005/034802 A3 | 4/2005 |
| WO | WO-2006/096805 A1 | 9/2006 |
| WO | WO-2006/110734 A2 | 10/2006 |
| WO | WO-2006/110734 A3 | 10/2006 |
| WO | WO-2006/115689 A1 | 11/2006 |
| WO | WO-2007/001936 A2 | 1/2007 |
| WO | WO-2007/001936 A3 | 1/2007 |
| WO | WO-2007/037516 A2 | 4/2007 |
| WO | WO-2007/037516 A3 | 4/2007 |
| WO | WO-2007/056502 A1 | 5/2007 |
| WO | WO-2008/017080 A2 | 2/2008 |
| WO | WO-2008/017080 A3 | 2/2008 |
| WO | WO-2008/036408 A2 | 3/2008 |
| WO | WO-2008/036408 A3 | 3/2008 |
| WO | WO-2008/091612 A2 | 7/2008 |
| WO | WO-2008/091612 A3 | 7/2008 |
| WO | WO-2008/121278 A2 | 10/2008 |
| WO | WO-2008/121278 A3 | 10/2008 |
| WO | WO-2008/150346 A1 | 12/2008 |
| WO | WO-2009/039191 A2 | 3/2009 |
| WO | WO-2009/039191 A3 | 3/2009 |
| WO | WO-2009/045265 A1 | 4/2009 |
| WO | WO-2009/094237 A1 | 7/2009 |
| WO | WO-2010/006061 A2 | 1/2010 |
| WO | WO-2010/006061 A3 | 1/2010 |
| WO | WO-2010/007600 A1 | 1/2010 |
| WO | WO-2010/048141 A2 | 4/2010 |
| WO | WO-2010/048141 A3 | 4/2010 |
| WO | WO-2010/115030 A1 | 10/2010 |
| WO | WO-2011/041488 A2 | 4/2011 |
| WO | WO-2011/041488 A3 | 4/2011 |
| WO | WO-2011/129893 A1 | 10/2011 |
| WO | WO-2011/129894 A2 | 10/2011 |
| WO | WO-2011/129894 A3 | 10/2011 |
| WO | WO-2012/170652 A1 | 12/2012 |
| WO | WO-2014/164028 A1 | 10/2014 |
| WO | WO-2015/066549 A1 | 5/2015 |
| WO | WO-2015/066549 A8 | 5/2015 |

OTHER PUBLICATIONS

Al-Saady, N.M. et al. (1999). "Left Atrial Appendage: Structure, Function, and Role in Thromboembolism," *Heart* 82:547-554.

Albers, G.W. (Jul. 11, 1994). "Atrial Fibrillation and Stroke: Three New Studies, Three Remaining Questions," *Arch Intern Med* 154:1443-1448.

Alonso, M. et al. (Mar. 4, 2003). "Complications With Femoral Access in Cardiac Catheterization. Impact of Previous Systematic Femoral Angiography and Hemostasis With VasoSeal-Es® Collagen Plug," *Rev. Esp. Cardiol.* 56(6):569-577.

(56) References Cited

OTHER PUBLICATIONS

Aronow, W.S. et al. (Apr. 2009). "Atrial Fibrillation: The New Epidemic of the Age-ing World," *Journal of Atrial Fibrillation* 1(6):337-361.

Babaliaros, V.C. et al. (Jun. 3, 2008). "Emerging Applications for Transseptal Left Heart Catheterization: Old Techniques for New Procedures," *Journal of the American College of Cardiology* 51(22):2116-2122.

Bath, P.M.W. et al. (2005). "Current Status of Stroke Prevention in Patients with Atrial Fibrillation," *European Heart Journal Supplements* 7(Supplement C):C12-C18.

Benjamin, B.A. et al. (1994). "Effect of Bilateral Atrial Appendectomy on Postprandial Sodium Excretion in Conscious Monkeys," *Society for Experimental Biology and Medicine* 206: 1 page.

Beygui, F. et al. (2005, e-pub. Oct. 21, 2005). "Multimodality Imaging of Percutaneous Closure of the Left Atrial Appendage," *Clinical Vignette*, 1 page.

Bisleri, G. et al. (Jun. 3, 2005). "Innovative Monolateral Approach for Closed-Chest Atrial Fibrillation Surgery," *The Annals of Thoracic Surgery* 80:e22-e25.

Björk, V.O. et al. (Aug. 1961). "Sequelae of Left Ventricular Puncture with Angiocardiography," *Circulation* 24:204-212.

Blackshear, J.L. et al. (Feb. 1996). "Appendage Obliteration to Reduce Stroke in Cardiac Surgical Patients With Atrial Fibrillation," *Ann. Thorac. Surg.* 61(2), 13 pages.

Blackshear, J.L. et al. (Oct. 1, 2003). "Thorascopic Extracardiac Obliteration of the Left Atrial Appendage for Stroke Risk Reduction in Atrial Fibrillation," *J. Am. Coll. Cardiol.* 42(7):1249-1252.

Bonanomi, G. et al. (Jan. 1, 2003). "Left Atrial Appendectomy and Maze," *Journal of the American College of Cardiology* 41(1):169-171.

Bonow, R.O. et al. (1998). "Guidelines for the Management of Patients With Valvular Heart Disease: Executive Summary: A Report of the American College of Cardiology/American Heart Association Task Force on Practice Guidelines (Committee on Management of Patients With Valvular Heart Disease)," *Circulation* 98:1949-1984.

Botham, R.J. et al. (May 1959). "Pericardial Tamponade Following Percutaneous Left Ventricular Puncture," *Circulation* 19:741-744.

Brock, R. et al. (1956). "Percutaneous Left Ventricular Puncture in the Assessment of Aortic Stenosis," *Thorax* 11:163-171.

Burke, R.P. et al. (1992). "Improved Surgical Approach to Left Atrial Appendage Aneurysm," *Journal of Cardiac Surgery* 7(2):104-107.

Canaccord Adams. (Aug. 11, 2008). "A-Fib: Near A Tipping Point," 167 pages.

Chung, M.K. (Jul. 2003). "Current Clinical Issues in Atrial Fibrillation," *Cleveland Clinic Journal of Medicine* 70(Supp. 3):S6-S11.

Coffin, L.H. (Jun. 1985). "Use of the Surgical Stapler to Obliterate the Left Atrial Appendage," *Surgery, Gynecology & Obstetric* 160:565-566.

Connolly, S.J. (Sep. 7, 1999). "Preventing Stroke in Atrial Fibrillation: Why Are So Many Eligible Patients Not Receiving Anticoagulant Therapy?" *Canadian Medical Association* 161(5):533-534.

Costa, R. et al. (2006). "Bi-Atrial Subxiphoid Epicardial Pacemaker in Superior Vena Cava Syndrome," *Arq. Bras. Cardiol.* 87:e45-e47.

Cox, J.L. et al. (Apr. 1991). "The Surgical Treatment of Atrial Fibrillation: IV. Surgical Technique," *J. Thorac. Cardiovasc. Surg.* 101(4):584-592.

Cox, J.L. et al. (Aug. 1995). "Modification of the Maze Procedure for Atrial Flutter and Atrial Fibrillation I. Rationale and Surgical Results," *J. Thorac. Cardiovasc. Surg.* 110(2):473-484.

Cox, J.L. et al. (Aug. 1995). "Modification of the Maze Procedure for Atrial Flutter and Atrial Fibrillation II. Surgical Technique of the Maze III Procedure," *J. Thorac. Cardiovasc. Surg.* 110(2):485-495.

Cox, J.L. et al. (Nov. 1999). "Impact of the Maze Procedure on the Stroke Rate in Patients with Atrial Fibrillation," *J. Thorac. Cardiovasc. Surg.* 118:833-840.

Cox, J.L. et al. (2004). "The Role of Surgical Intervention in the Management of Atrial Fibrillation," *Texas Heart Institute Journal* 31(3):257-265.

Crystal, E. et al. (Jan. 2003). "Left Atrial Appendage Occlusion Study (LAAOS): A Randomized Clinical Trial of Left Atrial Appendage Occlusion During Routine Coronary Artery Bypass Graft Surgery for Long-term Stroke Prevention," *Am Heart J* 145(1):174-178.

D'Avila, A. et al. (Apr. 2003). "Pericardial Anatomy for the Interventional Electrophysiologist," *Journal of Cardiovascular Electrophysiology* 14(4):422-430.

D'Avila, A. et al. (Nov. 2007). "Experimental Efficacy of Pericardial Instillation of Anti-inflammatory Agents During Percutaneous Epicardial Catheter Ablation to Prevent Postprocedure Pericarditis," *Journal of Cardiovascular Electrophysiology* 18(11):1178-1183.

Demaria, A.N. et al. (Dec. 17, 2003). "Highlights of the Year JACC 2003," *Journal of the American College of Cardiology* 42(12):2156-2166.

Deneu, S. et al. (Jul. 11, 1999). "Catheter Entrapment by Atrial Suture During Minimally Invasive Port-access Cardiac Surgery," *Canadian Journal of Anesthesia* 46(10):983-986.

Deponti, R. et al. (Mar. 7, 2006). "Trans-Septal Catheterization in the Electrophysiology Laboratory: Data From a Multicenter Survey Spanning 12 Years," *Journal of the American College of Cardiology* 47(5):1037-1042.

Donal, E. et al. (Sep. 2005). "The Left Atrial Appendage, a Small, Blind-Ended Structure: A Review of Its Echocardiographic Evaluation and Its Clinical Role," *Chest* 128(3):1853-1862.

Donnino, R. et al. (2007). "Left Atrial Appendage Thrombus Outside of a 'Successful' Ligation," *European Journal of Echocardiography* pp. 1-2.

Dullum, M.K.C. et al. (1999). "Xyphoid MIDCAB: Report of the Technique and Experience with a Less Invasive MIDCAB Procedure," *Heart Surgery Forum* 2(1):77-81.

Extended European Search Report dated Mar. 20, 2017, for EP Application No. 14 856 823.1, filed on Oct. 31, 2014, 8 pages.

Extended European Search Report dated Jul. 10, 2015, for European Patent Application No. 15153029.2, filed on Mar. 25, 2008, 6 pages.

Extended European Search Report dated Jun. 9, 2015, for EP Application No. 12 797 543.1, filed on Jun. 7, 2012, 6 pages.

Extended European Search Report dated Oct. 14, 2016, for EP Application No. 14 779 388.9 filed on Mar. 3, 2014, 7 pages.

Extended European Search Report dated Feb. 10, 2017, for EP Application No. 10 759 425.1, filed on Apr. 1, 2010, 7 pages.

Extended European Search Report dated Oct. 30, 2017, for EP Application No. 11 769 217.8, filed on Apr. 13, 2011, 12 pages.

Feinberg, W.M. et al. (Mar. 13, 1995). "Prevalence, Age Distribution, and Gender of Patients With Atrial Fibrillation," *Arch Intern Med* 155:469-473.

Fieguth, H.G. et al. (1997). "Inhibition of Atrial Fibrillation by Pulmonary Vein Isolation and Auricular Resection—Experimental Study in A Sheep Model," *European Journal of Cardio-Thoracic Surgery* 11:714-721.

Final Office Action dated Jun. 22, 2009, for U.S. Appl. No. 10/963,371, filed Oct. 11, 2004, 11 pages.

Final Office Action dated Apr. 14, 2010, for U.S. Appl. No. 11/600,671, filed Nov. 15, 2006, 7 pages.

Final Office Action dated Jul. 21, 2010, for U.S. Appl. No. 11/400,714, filed Apr. 7, 2006, 10 pages.

Final Office Action dated Apr. 26, 2011, for U.S. Appl. No. 12/037,802, filed Feb. 26, 2008, 9 pages.

Final Office Action dated Sep. 20, 2011, for U.S. Appl. No. 12/212,511, filed Sep. 17, 2008, 8 pages.

Final Office Action dated Oct. 28, 2011, for U.S. Appl. No. 12/055,213, filed Mar. 25, 2008, 15 pages.

Final Office Action dated May 4, 2012, for U.S. Appl. No. 12/363,359, filed Jan. 30, 2009, 10 pages.

Final Office Action dated May 16, 2012, for U.S. Appl. No. 12/363,381, filed Jan. 30, 2009, 8 pages.

Final Office Action dated Jul. 11, 2012, for U.S. Appl. No. 13/033,532, filed Feb. 23, 2011, 8 pages.

Final Office Action dated Jul. 24, 2012, for U.S. Appl. No. 12/212,511, filed Sep. 17, 2008, 6 pages.

(56) References Cited

OTHER PUBLICATIONS

Final Office Action dated Oct. 18, 2012, for U.S. Appl. No. 12/124,023, filed May 20, 2008, 15 pages.
Final Office Action dated Nov. 8, 2013, for U.S. Appl. No. 12/037,802, filed Feb. 26, 2008, 15 pages.
Final Office Action dated Jan. 13, 2014, for U.S. Appl. No. 12/752,873, filed Apr. 1, 2010, 10 pages.
Final Office Action dated Oct. 22, 2013 for U.S. Appl. No. 13/086,390, filed Apr. 13, 2011, 6 pages.
Final Office Action dated Aug. 12, 2014, for U.S. Appl. No. 13/033,532, filed Feb. 23, 2011, 6 pages.
Final Office Action dated Apr. 1, 2016, for U.S. Appl. No. 13/033,532, filed Feb. 23, 2011, 8 pages.
Final Office Action dated Nov. 14, 2014, for U.S. Appl. No. 12/363,359, filed Jan. 30, 2009, 10 pages.
Final Office Action dated Mar. 17, 2016, for U.S. Appl. No. 12/363,359, filed Jan. 30, 2009, 10 pages.
Final Office Action dated Nov. 18, 2015, for U.S. Appl. No. 13/490,919, filed Jun. 7, 2012, 10 pages.
Final Office Action dated Sep. 12, 2018, for U.S. Appl. No. 14/530,575, filed Oct. 31, 2014, 9 pages.
Final Office Action dated Aug. 11, 2014, for U.S. Appl. No. 13/086,389, filed Apr. 13, 2011, 16 pages.
Final Office Action dated Oct. 22, 2018, for U.S. Appl. No. 14/799,419, filed Jul. 14, 2015, 19 pages.
Fisher, D.C. et al. (Dec. 1998). "Large Gradient Across a Partially Ligated Left Atrial Appendage," *Journal of the American Society of Echocardiography* 11(12):1163-1165.
Friberg, L. et al. (2006). "Stroke Prophylaxis in Atrial Fibrillation: Who Gets it and Who Does Not?" *European Heart Journal* 27:1954-1964.
Friedman, P.A. et al. (Aug. 2009). "Percutaneous Epicardial Left Atrial Appendage Closure: Preliminary Results of an Electrogram Guided Approach," *Journal of Cardiovascular Electrophysiology* 20(8):908-915.
Fuster, V. et al. (Oct. 2001). "ACC/AHA/ESC Guidelines for the Management of Patients with Atrial Fibrillation," *European Heart Journal* 22(20):1852-1923.
Garcia-Fernandez, M.A. et al. (Oct. 1, 2003). "Role of Left Atrial Appendage Obliteration in Stroke Reduction in Patients With Mitral Valve Prosthesis," *Journal of the American College of Cardiology* 42(7):1253-1258.
Gardiner, G.A. Jr. et al. (Apr. 1986). "Complications of Transluminal Angioplasty," *Radiology* 159(1):201-208.
Gersak, Borut, et al. "European experience of the convergent atrial fibrillation procedure: multicenter outcomes in consecutive patients", J Thorac Cardiovasc Surg. Apr. 2014;147(4):1411-6. doi:10.1016/j.jtcvs.2013.06.057. Epub Aug. 26, 2013, 6 pages.
Gillinov, A.M. (Feb. 2007). "Advances in Surgical Treatment of Atrial Fibrillation," *Stroke* 38(part 2):618-623.
Gilman, R.A. et al. (Apr. 1963). "Direct Left Ventricular Puncture," *California Medicine* 98(4):200-203.
Goodwin, W.E. et al. (Nov. 1950). "Translumbar Aortic Puncture and Retrograde Catheterization of the Aorta In Aortography and Renal Arteriography," *Annals of Surgery* 132(5):944-958.
Gottlieb, L.K. et al. (Sep. 12, 1994). "Anticoagulation in Atrial Fibrillation," *Arch Intern Med.* 154:1945-1953.
Graffigna, A. et al. (1993). "Surgical Treatment of Wolff-Parkinson-White Syndrome: Epicardial Approach Without the Use of Cardiopulmonary Bypass," *J. Card. Surg.* 8:108-116.
Haissaguerre, M. et al. (Nov. 2005). "Catheter Ablation of Long-Lasting Persistent Atrial Fibrillation: Clinical Outcome and Mechanisms of Subsequent Arrhythmias," *Journal of Cardiovascular Electrophysiology* 16(11):1138-1147.
Halperin, J.L. et al. (Aug. 1988). "Atrial Fibrillation and Stroke: New Ideas, Persisting Dilemmas," *Journal of the American Heart Association* 19(8):937-941.
Halperin, J.L. et al. (Oct. 1, 2003). "Obliteration of the Left Atrial Appendage for Prevention of Thromboembolism," *Journal of the American College of Cardiology* 42(7):1259-1261.
Hammill, S.C. (May 2006). "Epicardial Ablation: Reducing the Risks," *J. Cardiovasc. Electrophysiol.* 17:550-552.
Hara, H. et al. (Jan. 2008). "Percutaneous Left Atrial Appendage Obliteration," *JACC: Cardiovascular Imagin* 1(1):92-93.
Hart, R.G. et al. (Nov. 2, 1999). "Atrial Fibrillation and Thromboembolism: A Decade of Progress in Stroke Prevention," *Annals of Internal Medicine* 131(9):688-695.
Hart, R.G. et al. (Mar. 2001). "Atrial Fibrillation and Stroke: Concepts and Controversies," *Stroke* 32:803-808.
Hart, R.G. (Sep. 11, 2003). "Atrial Fibrillation and Stroke Prevention," *The New England Journal of Medicine* 349(11):1015-1016.
Healey, J.S. et al. (Oct. 2003). "Surgical Closure of the Left Atrial Appendage for the Prevention of Stroke: A Randomized Pilot Trial of Safety and Efficacy (The Left Atrial Appendage Occlusion Study—LAAOS)," presented at The Canadian Cardiovascular Congress 2003, Toronto, Canada, Abstract No. 666, 2 pages.
Healey, J.S. et al. (Aug. 2005). "Left Atrial Appendage Occlusion Study (LAAOS): Results of a Randomized Controlled Pilot Study of Left Atrial Appendage Occlusion During Coronary Bypass Surgery in Patients At Risk for Stroke," *American Heart Journal* 150(2):288-293.
Hein, R. et al. (2005). "Patent Foramen Ovale and Left Atrial Appendage: New Devices and Methods for Closure," *Pediatric Cardiology* 26(3):234-240.
Heist, E.K. et al. (Nov. 2006). "Analysis of the Left Atrial Appendage by Magnetic Resonance Angiography in Patients with Atrial Fibrillation," *Heart Rhythm* 3(11):1313-1318.
Ho, I. et al. (Apr. 24, 2007). "Percutaneous Epicardial Mapping Ablation of a Posteroseptal Accessory Pathway," *Circulation* 115:e418-e421.
Ho, S.Y. et al. (Nov. 1999). "Anatomy of the Left Atrium: Implications for Radiofrequency Ablation of Atrial Fibrillation," *Journal of Cardiovascular Electrophysiology* 10(11):1525-1533.
Hoit, B.D. et al. (Jan. 1993). "Altered Left Atrial Compliance After Atrial Appendectomy. Influence on Left Atrial and Ventricular Filling," *Circulation Research* 72(1):167-175.
International Search Report dated Jul. 13, 2011, for PCT Patent Application No. PCT/US2011/000676, filed on Apr. 13, 2011, 2 pages.
International Search Report dated Mar. 26, 2015, for PCT Patent Application No. PCT/US2014/063570, filed on Oct. 31, 2014, 4 pages.
International Search Report dated May 19, 2008, for PCT Application No. PCT/US06/013459, filed on Apr. 7, 2006, 1 page.
International Search Report dated Feb. 27, 2007, for PCT Application No. PCT/US2008/003938, filed on Mar. 25, 2008, 5 pages.
International Search Report dated Jul. 30, 2010, for PCT Application No. PCT/US2008/076703, filed on Sep. 17, 2008, 2 pages.
International Search Report dated Jun. 1, 2010, for PCT Application No. PCT/US2010/029668, filed on Apr. 1, 2010, 2 pages.
International Search Report dated Sep. 14, 2012, for PCT Patent Application No. PCT/US2012/41285, filed on Jun. 7, 2012, 2 pages.
International Search Report dated Aug. 8, 2014, for PCT Application No. PCT/US2014/020030, filed on Mar. 3, 2014, 4 pages.
Inoue, Y. et al. (Jul.-Aug. 1997). "Video Assisted Thoracoscopic and Cardioscopic Radiofrequency Maze Ablation," *Asaio Journal* 43(4):334-337, Abstract Only.
Jaïs, P. et al. (2003). "Radiofrequency Ablation for Atrial Fibrillation," *European Society of Cardiology* 5(Supplement H):H34-H39.
Johnson, W.D. et al. (2000). "The Left Atrial Appendage: Our Most Lethal Human Attachment! Surgical Implications," *Euro. J. Cardiothoracic. Surg.* 17:718-722.
Jongbloed, M.R.M. et al. (2005). "Clinical Applications of Intracardiac Echocardiography in Interventional Procedures," *Heart* 91:981-990.
Kamohara, K. et al. (Aug. 2006). "Evaluation of a Novel Device for Left Atrial Appendage Exclusion: The Second-generation Atrial Exclusion Device," *The Journal of Thoracic and Cardiovascular Surgery* 132(2):340-346.
Kanderian, A.S. et al. (2008). "Success of Surgical Left Atrial Appendage Closure: Assessment by Transesophageal Echocardiography," *Journal of the American College of Cardiology* 52(11):924-929.

(56) References Cited

OTHER PUBLICATIONS

Kato, H. et al. (Aug. 1, 1996). "Evaluation of Left Atrial Appendage Stasis in Patients With Atrial Fibrillation Using Transesophageal Echocardiography With an Intravenous Albumin-Contrast Agent," *The American Journal of Cardiology* 78:365-369.

Katz, E.S. et al. (Aug. 2000). "Surgical Left Atrial Appendage Ligation is Frequently Incomplete: A Transesophageal Echocardiographic Study," *Journal of the American College of Cardiology* 36(2):468-471.

Kenner, H.M. et al. (Dec. 1966). "Intrapericardial, Intrapleural, and Intracardiac Pressures During Acute Heart Failure in Dogs Studied without Thoracotomy," *Circulation Research* 19:1071-1079.

Kerut, E.K. et al. (Jul. 2008). "Anatomy of the Left Atrial Appendage," *Echocardiography* 25(6):669-673.

Khargi, K. et al. (2005). "Surgical Treatment of Atrial Fibrillation: A Systematic Review," *European Journal of Cardiothoracic Surgery* 27:258-265.

Kim, K.B. et al. (Jan. 1998). "Effect of the Cox Maze Procedure on the Secretion of Atrial Natriuretic Peptide," *J. Thorac. Cardiovasc. Surg.* 115(1):139-146; discussion 146-147.

Kistler, P.M. et al. (May 2007). "The Left Atrial Appendage: Not Just an Innocent Bystander," *J. Cardiovasc Electrophysiol* 18(5):465-466.

Klein, H. et al. (Apr. 1990). "The Implantable Automatic Cardioverter-Defibrillator," *Herz* 15(2):111-125, Abstract Only.

Kolb, C. et al. (Feb. 2004). "Incidence of Antitachycardia Therapy Suspension Due to Magnet Reversion in Implantable Cardioverter Defibrillators," *Pace* 27:221-223.

Krikorian, J.G. et al. (Nov. 1978). "Pericardiocentesis," *Am. J. Med.* 65(5):808-814.

Krum, D. et al. (2004). "Visualization of Remnants of the left Atrial Appendage Following Epicardial Surgical Removal," *Heart Rhythm* 1:249.

Lacomis, J.M. et al. (Oct. 2003). "Multi-Detector Row CT of the Left Atrium and Pulmonary Veins before Radio-frequency Catheter Ablation for Atrial Fibrillation," *Radio Graphics* 23:S35-S48.

Lacomis, J.M. et al. (2007, e-pub. Oct. 17, 2007). "Dynamic Multidimensional Imaging of the Human Left Atrial Appendage," *Europace* 9:1134-1140.

Lee, R. et al. (1999). "The Closed Heart Maze: A Nonbypass Surgical Technique," *The Annals of Thoracic Surgery* 67:1696-1702.

Levinson, M.L. et al. (1998). "Minimally Invasive Atrial Septal Defect Closure Using the Subxyphoid Approach," *Heart Surg. Forum* 1(1):49-53, Abstract Only.

Lewis, D.R. et al. (1999). "Vascular Surgical Intervention for Complications of Cardiovascular Radiology: 13 Years' Experience in a Single Centre," *Ann. R. Coll. Surg. Engl.* 81:23-26.

Li, H. (2007). "Magnet Decoration, Beautiful But Potentially Dangerous For Patients with Implantable Pacemakers or Defibrillators," *Heart Rhythm* 4(1):5-6.

Lindsay, B.D. (1996). "Obliteration of the Left Atrial Appendage: A Concept Worth Testing," *The Annals of Thoracic Surgery* 61:515-516.

Lip, G.Y.H. et al. (Jun. 2001). "Thromboprophylaxis for Atrial Flutter," *European Heart Journal* 22(12):984-987.

Lustgarten, D.L. et al. (May/Jun. 1999). "Cryothermal Ablation: Mechanism of Tissue Injury and Current Experience in the Treatment of Tachyarrhthmias," *Progress in Cardiovascular Diseases* 41(6):481-498.

Macris, M. et al. (Jan. 1999). "Minimally Invasive Access of the Normal Pericardium: Initial Clinical Experience with a Novel Device," *Clin. Cardiol.* 22(Suppl. I):I-36-I-39.

Maisch, B. et al. (Jan. 1999). "Intrapreicardial Treatment of Inflammatory and Neoplastic Pericarditis Guided by Pericardioscopy and Epicardial Biopsy—Results from a Pilot Study," *Clin. Cardiol.* 22(Supp. I):I-17-I-22.

Mannam, A.P. et al. (Apr. 1, 2002). "Safety of Subxyphoid Pericardial Access Using a Blunt-Tip Needle," *The American Journal of Cardiology* 89:891-893.

Mattox, K.L. et al. (May 1997). "Newer Diagnostic Measure and Emergency Management," *Ches Surg Clin N Am.* 7(2):213-226, Abstract Only.

Mccarthy, P.M. et al. (2008). "Epicardial Atrial Fibrillation Ablation," Chapter 23 in *Contemporary Cardiology: Atrial Fibrillation, From Bench to Bedside*, Natale, A. et al. eds.,. Humana Press,: Totowa, NJ, pp. 323-332.

Mccaughan, J.J. Jr., et al. (Nov. 1957). "Aortography Utilizing Percutaneous Left Ventricular Puncture," located at <http://www.archsurg.com>, last visited on Apr. 7, 2009, 73:746-751.

Mcclelland, R.R. (1978). "Congenital Aneurysmal Dilatation of the Left Auricle Demonstrated by Sequential Cardiac Blood-Pool Scintiscanning," *J. Nucl. Med.* 19(5):507-509.

Melo, J. et al. (Apr. 21, 2008). "Surgery for Atrial Fibrillation in Patients with Mitral Valve Disease: Results at Five Years from the International Registry of Atrial Fibrillation Surgery," *The Journal of Thoracic and Cardiovascular Surgery* 135(4):863-869.

Miller, P.S.J. et al. (Feb. 2005). "Are Cost Benefits of Anticoagulation for Stroke Prevention in Atrial Fibrillation Underestimated?" *Stroke* 36:360-366.

Miyasaka, Y. et al. (Jul. 11, 2006). "Secular Trends in Incidence of Atrial Fibrillation in Olmsted County, Minnesota, 1980 to 2000, and Implications on the Projections for Future Prevalence," *Circulation* 114:119-125.

Morris, J.J. Jr. (1979). "Transvenous versus Transthoracic Cardiac Pacing," Chapter 16 in *Cardiac Pacing: A Concise Guide to Clinical Practice*, pp. 239-245.

Mráz, T. et al. (Apr. 2007). "Role of Echocardiography in Percutaneous Occlusion of the left Atrial Appendage," *Echocardiography* 24(4):401-404.

Naclerio, E.A. et al. (1979). "Surgical Techniques for Permanent Ventricular Pacing," Chapter 10 in *Cardiac Pacing: A Concise Guide to Clinical Practice*, pp. 145-168.

Nakai, T. et al. (May 7, 2002). "Percutaneous Left Atrial Appendage Occlusion (PLAATO) for Preventing Cardioembolism: First Experience in Canine Model," *Circulation* 105:2217-2222.

Nakajima, H. et al. (2004). "Consequence of Atrial Fibrillation and the Risk of Embolism After Percutaneous Mitral Commissurotomy: The Necessity of the Maze Procedure," *The Annals of Thoracic Surgery* 78:800-806.

Non-Final Office Action dated Feb. 5, 2014 for U.S. Appl. No. 13/086,389, filed Apr. 13, 2011, 16 pages.

Non-Final Office Action dated Mar. 13, 2008 for U.S. Appl. No. 10/963,371, filed Oct. 11, 2004, 14 pages.

Non-Final Office Action dated Aug. 6, 2008 for U.S. Appl. No. 10/963,371, filed Oct. 11, 2004, 14 pages.

Non-Final Office Action dated Jun. 26, 2009, for U.S. Appl. No. 11/600,671, filed Nov. 15, 2006, 9 pages.

Non-Final Office Action dated Dec. 30, 2009, for U.S. Appl. No. 11/400,714, filed Apr. 7, 2006, 8 pages.

Non-Final Office Action dated Jul. 22, 2010, for U.S. Appl. No. 12/037,802, filed Feb. 26, 2008, 10 pages.

Non-Final Office Action dated Nov. 15, 2010, for U.S. Appl. No. 12/055,213, filed Mar. 25, 2008, 18 pages.

Non-Final Office Action dated Feb. 17, 2011, for U.S. Appl. No. 12/212,511, filed Sep. 17, 2008, 14 pages.

Non-Final Office Action dated Apr. 28, 2011, for U.S. Appl. No. 12/055,213, filed Mar. 25, 2008, 20 pages.

Non-Final Office Action dated Oct. 27, 2011, for U.S. Appl. No. 12/363,359, filed Jan. 30, 2009, 11 pages.

Non-Final Office Action dated Nov. 9, 2011, for U.S. Appl. No. 12/363,381, filed Jan. 30, 2009, 10 pages.

Non-Final Office Action dated Dec. 22, 2011, for U.S. Appl. No. 13/033,532, filed Feb. 23, 2011, 8 pages.

Non-Final Office Action dated Mar. 7, 2012, for U.S. Appl. No. 12/124,023, filed May 20, 2008, 13 pages.

Non-Final Office Action dated Apr. 2, 2012, for U.S. Appl. No. 12/212,511, filed Sep. 17, 2008, 5 pages.

Non-Final Office Action dated Sep. 18, 2013, for U.S. Appl. No. 12/055,213, filed Mar. 25, 2008, 15 pages.

Non-Final Office Action dated May 31, 2013, for U.S. Appl. No. 12/124,023, filed May 20, 2008, 14 pages.

(56) References Cited

OTHER PUBLICATIONS

Non-Final Office Action dated Apr. 2, 2014, for U.S. Appl. No. 13/033,532, filed Feb. 23, 2011, 8 pages.
Non-Final Office Action dated Jun. 17, 2014, for U.S. Appl. No. 12/363,359, filed Jan. 30, 2009, 7 pages.
Non-Final Office Action dated May 3, 2013 for U.S. Appl. No. 13/086,390, filed Apr. 13, 2011, 10 pages.
Non-Final Office Action dated Jan. 15, 2015, for U.S. Appl. No. 13/086,389, filed Apr. 13, 2011, 16 pages.
Non-Final Office Action dated Jan. 16, 2013, for U.S. Appl. No. 12/037,802, filed Feb. 26, 2008, 10 pages.
Non-Final Office Action dated May 4, 2015, for U.S. Appl. No. 12/124,023, filed May 20, 2008, 8 pages.
Non-Final Office Action dated Oct. 28, 2015, for U.S. Appl. No. 13/033,532, filed Feb. 23, 2011, 9 pages.
Non-Final Office Action dated Sep. 10, 2015, for U.S. Appl. No. 12/363,359, filed Jan. 30, 2009, 13 pages.
Non-Final Office Action dated Mar. 29, 2013, for U.S. Appl. No. 12/752,873, filed Apr. 1, 2010, 16 pages.
Non-Final Office Action dated Dec. 2, 2016, for U.S. Appl. No. 14/625,540, filed Feb. 18, 2015, 20 pages.
Non-Final Office Action dated Dec. 2, 2015, for U.S. Appl. No. 14/309,835, filed Jun. 19, 2014, 8 pages.
Non-Final Office Action dated Nov. 10, 2014, for U.S. Appl. No. 12/752,873, filed Apr. 1, 2010, 10 pages.
Non-Final Office Action dated Mar. 31, 2015, for U.S. Appl. No. 13/490,919, filed Jun. 7, 2012, 14 pages.
Non-Final Office Action dated Aug. 9, 2017, for U.S. Appl. No. 14/530,575, filed Oct. 31, 2014, 8 pages.
Non-Final Office Action dated Jan. 23, 2018, for U.S. Appl. No. 14/530,575, filed Oct. 31, 2014, 8 pages.
Non-Final Office Action dated Feb. 22, 2018, for U.S. Appl. No. 14/799,419, filed Jul. 14, 2015, 17 pages.
Notice of Allowance dated Mar. 20, 2014 for U.S. Appl. No. 13/086,390, filed Apr. 13, 2011, 8 pages.
Notice of Allowance dated Sep. 17, 2010, for U.S. Appl. No. 10/963,371, filed Oct. 11, 2004, 7 pages.
Notice of Allowance dated Sep. 17, 2010, for U.S. Appl. No. 11/600,671, filed Nov. 15, 2006, 7 pages.
Notice of Allowance dated Nov. 24, 2010, for U.S. Appl. No. 11/400,714, filed Apr. 7, 2006, 8 pages.
Notice of Allowance dated Feb. 22, 2013, for U.S. Appl. No. 12/212,511, filed Sep. 17, 2008, 8 pages.
Notice of Allowance dated Mar. 18, 2013, for U.S. Appl. No. 12/212,511, filed Sep. 17, 2008, 6 pages.
Notice of Allowance dated Mar. 4, 2014, for U.S. Appl. No. 12/055,213, filed Mar. 25, 2008, 9 pages.
Notice of Allowance dated Apr. 1, 2014, for U.S. Appl. No. 12/363,381, filed Jan. 30, 2009, 9 pages.
Notice of Allowance dated Apr. 3, 2014, for U.S. Appl. No. 12/037,802, filed Feb. 26, 2008, 8 pages.
Notice of Allowance dated Jul. 11, 2016, for U.S. Appl. No. 14/309,835, filed Jun. 19, 2014, 5 pages.
Notice of Allowance dated Jan. 18, 2019, for U.S. Appl. No. 14/799,419, filed Jul. 14, 2015, 8 pages.
Notice of Allowance dated Apr. 26, 2019, for U.S. Appl. No. 14/799,419, filed Jul. 14, 2015, 9 pages.
Notice of Allowance dated Jun. 5, 2020, for U.S. Appl. No. 16/289,365, filed Feb. 28, 2019. 7 pages.
Odell, J.A. et al. (1996). "Thorascopic Obliteration of the Left Atrial Appendage: Potential for Stroke Reduction?" *Ann. Thorac. Surg.* 61:565-569.
O'Donnell, M. et al. (2005). "Emerging Therapies for Stroke Prevention in Atrial Fibrillation," *European Heart Journal* 7(Supplement C):C19-C27.
Omran, H. et al. (1997). "Left Atrial Appendage Function in Patients with Atrial Flutter," *Heart* 78:250-254.
Onalan, O. et al. (2005). "Nonpharmacologic Stroke Prevention in Atrial Fibrillation," *Expert Rev. Cardiovasc. Ther.* 3(4):619-633.

Onalan, O. et al. (2007). "Left Atrial Appendage Exclusion for Stroke Prevention in Patients With Nonrheumatic Atrial Fibrillation," *Stroke* 38(part 2):624-630.
Ostermayer, S. et al. (2003). "Percutaneous Closure of the Left Atrial Appendage," *Journal of Interventional Cardiology* 16(6):553-556.
Ota, T. et al. (2006). "Epicardial Atrial Ablation Using a Novel Articulated Robotic Medical Probe Via a Percutaneous Subxiphoid Approach," *National Institute of Health* 1(6):335-340.
Ota, T. et al. (Oct. 2007). "Impact of Beating Heart left Atrial Ablation on Left-sided Heart Mechanics," *The Journal of Thoracic and Cardiovascular Surgery* 134(4):982-988.
Pennec, P-Y. et al. (2003). "Assessment of Different Procedures for Surgical Left Atrial Appendage Exclusion," *The Annals of Thoracic Surgery* 76:2167-2168.
Perk, G. et al. (Aug. 2009). "Use of Real Time Three-Dimensional Transesophageal Echocardiography in Intracardiac Catheter Based Interventions," *J. Am Soc Echocardiogr* 22(8):865-882.
Pollick C. (Feb. 2000). "Left Atrial Appendage Myopathy," *Chest* 117(2):297-308.
Poulsen, T.S. et al. (Feb. 15, 2005). "Is Aspirin Resistance or Female Gender Associated With a High Incidence of Myonecrosis After Nonurgent Percutaneous Coronary Intervention?" *J. Am. Coll. Cardiol.* 45(4):635-636.
Reznik, G. et al. (Oct. 1992). "Percutaneous Endoscopic Implantation of Automatic Implantable Cardioverter/Defibrillator (AICD): An Animal Study of a New Nonthoracotomy Technique," *J. Laparoendosc. Surg.* 2(5):255-261, Abstract Only.
Robicsek, F. (1987). "Closed-Chest Decannulation of Transthoracically Inserted Aortic Balloon Catheter without Grafting," *Journal of Cardiac Surgery* 2(2):327-329.
Ross, J. Jr. et al. (Jun. 3, 2008). "Transseptal Left Heart Catheterization: A 50-Year Odyssey," *Journal of the American College of Cardiology* 51(22):2107-2115.
Rubin, D.N. et al. (Oct. 1, 1996). "Evaluation of Left Atrial Appendage Anatomy and Function in Recent-Onset Atrial Fibrillation by Transesophageal Echocardiography," *Am J Cardiol* 78:774-778.
Ruchat, P. et al. (2002). "Off-pump Epicardial Compartmentalization for Ablation of Atrial Fibrillation," *Interactive Cardio Vascular and Thoracic Surgery* 1:55-57.
Salzberg, S.P. et al. (2008). "Surgical Left Atrial Appendage Occlusion: Evaluation of a Novel Device with Magnetic Resonance Imaging," *European Journal of Cardiothoracic Surgery* 34:766-770.
Sapp, J. et al. (Dec. 2001). "Electrophysiology and Anatomic Characterization of an Epicardial Accessory Pathway," *Journal of Cardiovascular Electrophysiology* 12(12):1411-1414.
Scharf, C. et al. (2005). "Catheter Ablation for Atrial Fibrillation: Pathophysiology, Techniques, Results and Current Indications," *Continuous Medical Education* 8:53-61.
Scherr, D. et al. (Apr. 2009). "Incidence and Predictors of left Atrial Thrombus Prior to Catheter Ablation of Atrial Fibrillation," *Journal of Cardiovascular Electrophysiology* 20(4):379-384.
Schmidt, H. et al. (Sep. 2001). "Prevalence of Left Atrial Chamber and Appendage Thrombi in Patients With Atrial Flutter and Its Clinical Significance," *Journal of the American College of Cardiology* 38(3):778-784.
Schneider, B. et al. (2005, e-pub. Aug. 22, 2005). "Surgical Closure of the Left Atrial Appendage—A Beneficial Procedure?" *Cardiology* 104:127-132.
Schweikert, R.A. et al. (Sep. 16, 2003). "Percutaneous Pericardial Instrumentation for Endo-Epicardial Mapping of Previously Failed Ablation," *Circulation* 108:1329-1335.
Schweikert, R.A. et al. (2005). "Epicardial Access: Present and Future Applications for Interventional Electrophysiologists," Chapter 25 in *New Arrhythmia Technolgies*, Wang, P.J. ed., Blackwell Publishing, pp. 242-256.
Seferovic, P. et al. (Jan. 1999). "Initial Clinical Experience with the PerDUCER® Device: Promising New Tool in the Diagnosis and Treatment of Pericardial Disease," *Clin. Cardiol.* 22(Supp I):I-30-I-35.

(56) References Cited

OTHER PUBLICATIONS

Sengupta, P.P. et al. (2005). "Transoesophageal Echocardiography," *Heart* 91:541-547.

Sharada, K. et al. (2005). "Non-Surgical Transpericardial Catheter Ablation of Post-Infarction Ventricular Tachycardia," *Indian Heart J* 57:58-61.

Sievert, H. et al. (Apr. 23, 2002). "Percutaneous Left Atrial Appendage Transcatheter Occlusion to Prevent Stroke in High-Risk Patients With Atrial Fibrillation," *Circulation* 105:1887-1889.

Singer, D.E. et al. (Sep. 2004). "Antithrombotic Therapy in Atrial Fibrillation: The Seventh ACCP Conference on Antithrombotic and Thrombolytic Therapy," *Chest* 126(3):429S-456S.

Smith, P.W. et al. (Nov. 1956). "Diagnosis of Mitral Regurgitation by Cardioangiography," *Circulation* 14:847-853.

Soejima, K. et al. (2004). "Subxiphoid Surgical Approach for Epicardial Catheter-Based Mapping and Ablation in Patients With Prior Cardiac Surgery or Difficult Pericardial Access," *Circulation* 110:1197-1201.

Sosa, E. et al. (1996). "A New Technique to Perform Epicardial Mapping in the EP Laboratory," *J. Cardiovasc. Electrophysiol.* 7(6):531-536.

Sosa, E. et al. (Mar. 1998). "Endocardial and Epicardial Ablation Guided by Nonsurgical Transthoracic Epicardial Mapping to Treat Recurrent Ventricular Tachycardia," *J. Cardiovasc. Elecytophysiol.* 9(3):229-239.

Sosa, E. et al. (Dec. 14, 1999). "Different Ways of Approaching the Normal Pericardial Space," *Circulation* 100(24):e115-e116.

Sosa, E. et al. (Jul. 15, 2002). "Gaining Access to the Pericardial Space," *The American Journal of Cardiology* 90:203-204.

Sosa, E. et al. (Apr. 2005). "Epicardial Mapping and Ablation Techniques to Control Centricular Tachycardia," *Journal of Cardiovasc. Electrphsiol.* 16(4):449-452.

Sparks, P.B. et al. (2001). "Is Atrial Flutter a Risk Factor for Stroke?" *Journal of the American College of Cardiology* 38(3):785-788.

Spodick, D.H. (Nov. 1970). "Medical History of the Pericardium," *The American Journal of Cardiology* 26:447-454.

Stewart, J.M. et al. (Apr. 1992). "Bilateral Atrial Appendectomy Abolishes Increased Plasma Atrial Natriuretic Peptide Release and Blunts Sodium and Water Excretion During Volume Loading in Conscious Dogs," *Circulation Research* 70(4):724-732.

Stewart, S. (1974). "Placement of the Sutureless Epicardial Pacemaker Lead by the Subxiphoid Approach," *Ann. Of Thoracic Surg.* 18(3):308-313.

Stoddard, M.F. et al. (1995). "Left Atrial Appendage Thrombus is not Uncommon in Patients with Acute Atrial Fibrillation and a Recent Embolic Event: A Transesophageal Echocardiographic Study," *J. Am. Coll. Cardiol.* 25:452-459, Abstract Only.

Stokes, K. (Jun. 1990). "Implantable Pacing Lead Technology," *IEEE Engineering in Medicine and Biology* pp. 43-49.

Stöllberger, C. et al. (2000). "Is the Left Atrial Appendage Our Most Lethal Attachment?" *European Journal of Cardio-Thoracic Surgery* 18:625-626.

Stöllberger, C. et al. (Dec. 2003). "Elimination of the Left Atrial Appendage To Prevent Stroke or Embolism ?: Anatomic, Physiologic, and Pathophysiologic Considerations," 124(6):2356-2362.

Stöllberger, C. et al. (2006). "Stroke Prevention by Means of Epicardial Occlusion of the Left Atrial Appendage," *Journal of Thoracic and Cardiovascular Surgery* 132(1):207-208.

Stöllberger, C. et al. (2007). "Arguments Against Left Atrial Appendage Occlusion for Stroke Prevention," *Stroke* 38:e77.

Stöllberger, C. et al. (2007). "Leave the Left Atrial Appendage Untouched for Stroke Prevention!" *Journal of Thoracic and Cardiovascular Surgery* 134(2):549-550.

Su, P. et al. (Sep. 2008, e-pub. May 8, 2007). "Occluding the Left Atrial Appendage: Anatomical Considerations," *Heart* 94(9):1166-1170.

Subramanian, V.A. (Jun. 1997). "Less Invasive Arterial CABG on a Beating Heart," *Ann. Thorac. Surg.* 63(6 Suppl.):S68-S71.

Subramanian, V.A. et al. (Dec. 1997). "Minimally Invasive Direct Coronary Artery Bypass Grafting: Two-Year Clinical Experience," *Ann. Thorac. Surg.* 64(6):1648-1653, Abstract Only.

Suehiro, S. et al. (1996). "Echocardiography-Guided Pericardiocentesis With a Needle Attached to a Probe," *Ann. Thoracic Surg.* 61:741-742.

Sun, F. et al. (Feb. 2006). "Subxiphoid Access to Normal Pericardium with Micropuncture Set: Technical Feasibility Study in Pigs," *Radiology* 238(2):719-724.

Supplementary Search Report dated Mar. 14, 2011, for EP Application No. 04 794 730.4, filed on Oct. 11, 2004, 4 pages.

Szili-Torok, T. et al. (2001). "Transseptal Left heart Catheterisation Guided by Intracardiac Echocardiography," *Heart* 86:e11-e15.

Tabata, T. et al. (Feb. 1, 1998). "Role of Left Atrial Appendage in left Atrial Reservoir Function as Evaluated by Left Atrial Appendage Clamping During Cardiac Surgery," *The American Journal of Cardiology* 81:327-332.

Tomar, M. et al. (Jul.-Aug. 2006). "Transcatheter Closure of Fossa Ovalis Atrial Septal Defect: A Single Institutional Experience," *Indian Heart Journal* 58(4):325-329.

Troughton, R.W. et al. (Feb. 28, 2004). "Pericarditis," *The Lancet* 363:717-727.

Ulicny K.S. et al. (Jun. 1992). "Conjoined Subrectus Pocket for Permanent Pacemaker Placement in the Neonate," *Ann Thorac Surg.* 53(6):1130-1131, Abstract Only.

Valderrabano, M. et al. (Sep. 2004). "Percutaneous Epicardial Mapping During Ablation of Difficult Accessory Pathways as an Alternative to Cardiac Surgery," *Heart Rhythm* 1(3):311-316.

Von Korn, H. et al. (2006). "Simultaneous Combined Interventional Percutaneous Left Atrial Auricle and Atrial Septal Defect Closure," *Heart* 92:1462.

Wang, T.J. et al. (Aug. 27, 2003). "A Risk Score for Predicting Stroke or Death in Individuals With New-Onset Atrial Fibrillation in the Community," *American Medical Association* 290(8):1049-1056.

Watkins, L. et al. (Nov. 1982). "Implantation of the Automatic Defibrillator: The Subxiphoid Approach," *Ann. of Thoracic Surg.* 34(5):515-520.

W.L. Gore & Associates (Aug. 11, 2006). "Gore Helex™ Septal Occluder," located at <http://www.fda.gov/cdrh/pdf5/p050006a.pdf>, last visited on Jun. 14, 2007, 3 pages.

Wolber, T. et al. (Jan. 2007). "Potential Interference of Small Neodymium Magnets with Cardiac pacemakers and Implantable Cardioverter-defibrillators," *Heart Rhythm* 4(1):1-4.

Wolf, P.A. et al. (Oct. 1978). "Epidemiologic Assessment of Chronic Atrial Fibrillation and Risk of Stroke: The Fiamingham Study," *Neurology* 28:973-977.

Wolf, P.A. et al. (Aug. 1991). "Atrial Fibrillation as an Independent Risk Factor For Stroke: The Framingham Study," *Stroke* 22(8):983-988.

Wolf, P.A. et al. (Feb. 9, 1998). "Impact of Atrial Fibrillation on Mortality, Stroke, and Medical Costs," *Arch Intern Med* 158:229-234.

Wong, J.W.W. et al. (2006). "Impact of Maze and Concomitant Mitral Valve Surgery on Clinical Outcomes," *The Annals of Thoracic Surgery* 82:1938-1947.

Wongcharoen, W. et al. (Sep. 2006). "Morphologic Characteristics of the Left Atrial Appendage, Roof, and Septum: Implications for the Ablation of Atrial Fibrillation," *Journal of Cardiovascular Electrophysiology* 17(9):951-956.

Wood, M.A. (Jan. 2006). "Percutaneous Pericardial Instrumentation in the Electrophysiology Laboratory: A Case of Need," *Heart Rhythm* 3(1):11-12.

Written Opinion of the International Searching Authority dated Jul. 13, 2011, for PCT Patent Application No. PCT/US2011/000676, filed on Apr. 13, 2011, 6 pages.

Written Opinion of the International Searching Authority dated Mar. 26, 2015, for PCT Patent Application No. PCT/US2014/063570, filed on Oct. 31, 2014, 6 pages.

Written Opinion dated May 19, 2008, for PCT Application No. PCT/US06/013459, filed on Apr. 7, 2006, 6 pages.

(56) References Cited

OTHER PUBLICATIONS

Written Opinion of the International Searching Authority dated Feb. 27, 2007, for PCT Application No. PCT/US2008/003938, filed on Mar. 25, 2008, 10 pages.
Written Opinion of the International Searching Authority dated Jul. 30, 2010, for PCT Application No. PCT/US2008/076703, filed on Sep. 17, 2008, 8 pages.
Written Opinion of the International Searching Authority dated Jun. 1, 2010, for PCT Application No. PCT/US2010/029668, filed on Apr. 1, 2010, 8 pages.
Written Opinion of the International Search Authority dated Oct. 3, 2011, for PCT Application No. PCT/US2011/00677, filed on Apr. 13, 2011, 6 pages.
Written Opinion from the International Searching Authority dated Sep. 14, 2012, for PCT Patent Application No. PCT/US2012/41285, filed on Jun. 7, 2012; 6 pages.
Written Opinion of the International Searching Authority dated Aug. 8, 2014, for PCT Application No. PCT/US2014/020030, filed on Mar. 3, 2014, 6 pages.
Wudel, J.H. et al. (Apr. 3, 2008). "Video-Assisted Epicardial Ablation and left Atrial Appendage Exclusion for Atrial Fibrillation: Extended Follow-Up," *The Annals of Thoracic Surgery* 85:34-38.
Wyse, D.G. et al. (Dec. 5, 2002). "Of 'Left Atrial Appendage Amputation, Ligation, or Occlusion In Patients with Atrial Fibrillation'," *N Engl J Med* 347(23):1825-1833, Abstract Only.
Yamada, Y. et al. (Aug. 2006). "Video-Assisted Thoracoscopy to Treat Atrial Tachycardia Arising from Left Atrial Appendage," *Journal of Cardiovascular Electrophysiology* 17(8):895-898.
Zapolanski, A. et al. (May 2008). "Safe and Complete Exclusion of the left Atrial Appendage, A Simple Epicardial Approach," *Innovations* 3(3):161-163.
Zenati, M.A. et al. (Sep. 2003). "Left Heart Pacing Lead Implantation Using Subxiphoid Videopericardioscopy," *Journal of Cardiovascular Electrophysiology* 14(9):949-953.
Zenati, M.A. et al. (2004). "Mechanical Function of the Left Atrial Appendage Following Epicardial Bipolar Radiofrequency Ablation," *Cardiothoracic Techniques and Technologies X*, Abstract 121A, p. 176.
Zenati, M.A. et al. (2005). "Modification of the Left Atrial Appendage," Chapter 12 in *Innovative Management of Atrial Fibrillation*, Schwartzman, David ed., Blackwell Science Ltd., 5 pages.

\* cited by examiner

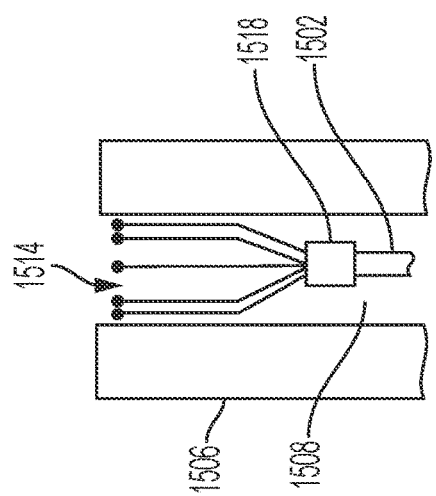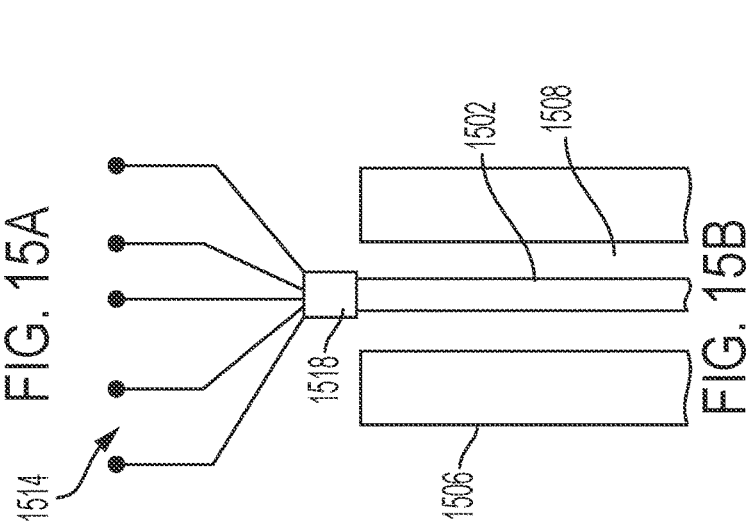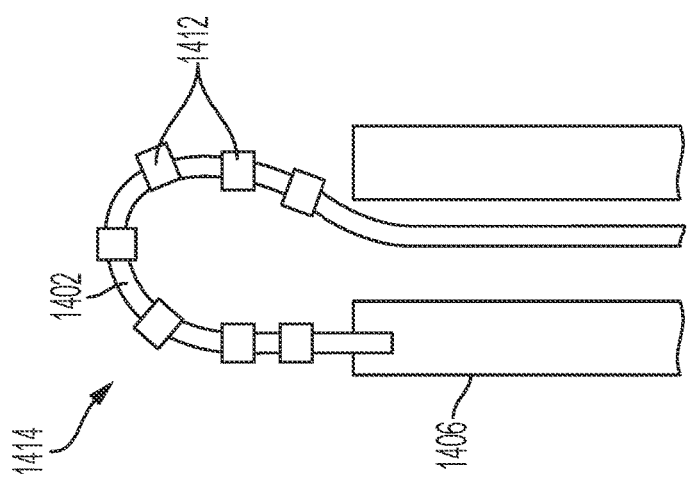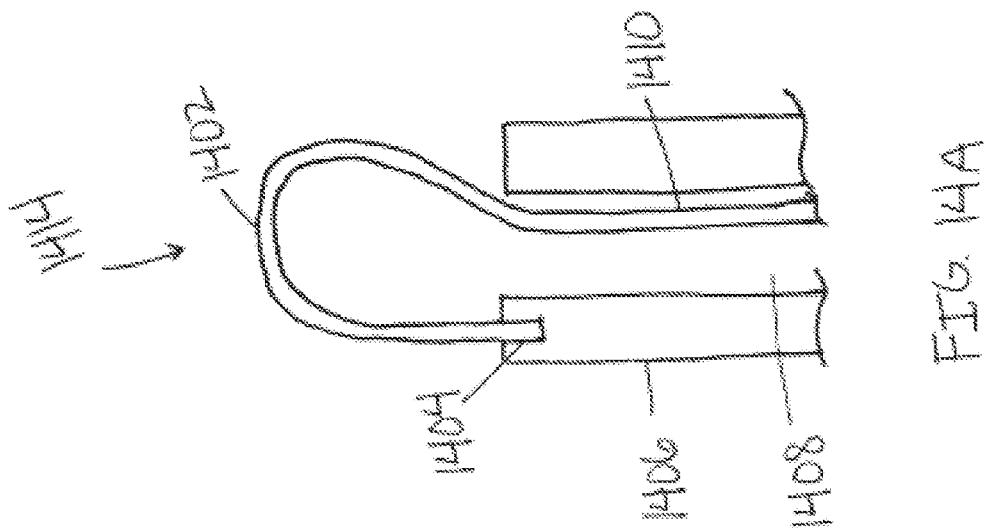

DEVICES AND METHODS FOR LEFT ATRIAL APPENDAGE CLOSURE

CROSS-REFERENCE TO RELATED APPLICATIONS

This application is a continuation application of U.S. patent application Ser. No. 16/289,365, filed on Feb. 28, 2019, now U.S. Pat. No. 10,799,288, issued on Oct. 13, 2020, which is a continuation application of U.S. patent application Ser. No. 14/530,575, filed on Oct. 31, 2014, now U.S. Pat. No. 10,258,408, issued Apr. 16, 2019, which claims priority to U.S. Provisional Patent Application Ser. No. 61/898,382, filed on Oct. 31, 2013, each of which is incorporated by reference herein in its entirety.

FIELD

This invention relates generally to systems and methods for closing tissue such as the left atrial appendage.

BACKGROUND

Atrial fibrillation is a common problem that afflicts millions of patients. Atrial fibrillation often results in the formation of a thrombus, or clot, in the appendage of the left atrium. This presents a problem, inasmuch as the thrombus can dislodge and embolize to distant organs, which may result in adverse events such as a stroke. For this reason, most patients with atrial fibrillation are treated with one or more blood thinners to help prevent the formation of a thrombus. Blood thinners, however, can present health risks of their own, especially in the elderly. These risks, such as bleeding, often require a user to make significant lifestyle changes.

Several methods have been developed to address the potential problem of thrombus formation in the left atrial appendage. One such method includes stunting the left atrial appendage along the base or ostial neck where it joins the atrial chamber. In this way, blood flow into the atrial appendage is cut off, eliminating the risk of thrombus formation therein. This is typically done through open-heart surgery, which limits the availability of the procedure to those who are at a particularly high risk, or who are otherwise undergoing an open-heart procedure. In addition, open-heart surgery requires general anesthesia and has a number of well-known risks, making it less desirable.

Other methods have also been investigated. These methods include methods of stapling the base of the appendage and methods of filling the appendage with a space occupying or occluding member. Stapling is not preferred given the fragility of the appendage and its tendency to rupture, while occlusion devices may not effectively prevent all blood flow into the appendage.

Additional devices and methods for closing the left atrial appendage or other suitable tissues would therefore be desirable. In particular, devices and methods for closing the left atrial appendage using minimally invasive, intravascular, or a combination of these techniques, would be desirable in order to avoid the need for opening the chest. Of course, additional devices for use in open surgical procedures are desirable as well, especially when those devices offer additional advantages over standard devices.

BRIEF SUMMARY

Described here are devices, systems, and methods for closing an atrial appendage such as the left atrial appendage. In some instances, the methods described here may comprise positioning a balloon at least partially within an interior of the atrial appendage and positioning a closure assembly of a closure device around an exterior of the atrial appendage. The methods may further comprise inflating the balloon at least partially within the interior of the atrial appendage, and partially closing the closure assembly to pull interior tissue of the atrial appendage into contact with the inflated balloon. In some of these variations, the methods may further comprise ablating the interior tissue of the atrial appendage with the inflated balloon, removing the balloon from the atrial appendage, and closing the atrial appendage with the closure assembly.

In some variations, the method may further comprise positioning a distal end of a first guide element in the interior of the atrial appendage and positioning a distal end of a second guide element in a pericardial space externally of the atrial appendage. In some instances, the first guide element and the second guide element may each comprise a magnet, and the method may further comprise aligning the first guide element and the second guide element across tissue of the atrial appendage. In some variations, positioning the closure device may include advancing the closure device along the second guide element. The balloon may be part of the first guide element, or may be part of a balloon catheter. In instances where the balloon is part of the balloon catheter, positioning the balloon may comprise advancing the balloon catheter along the first guide element.

In some variations the balloon may comprise an electrode positioned on an exterior surface of the balloon, and ablating the interior tissue of the atrial appendage may comprise ablating the interior tissue of the atrial appendage with the electrode. In other variations, the balloon may comprise at least two electrodes and the method may further comprise monitoring a tissue parameter with at least one of the electrodes during ablation of the interior tissue. In yet other variations, ablating the interior tissue of the atrial appendage may comprise ablating the interior tissue of the atrial appendage using heated fluid contained in the balloon. In some variations the method may further comprise releasing a suture loop from the closure assembly to hold the atrial appendage closed. Additionally or alternatively, in some variations the closure assembly may comprise an electrode, and the method may further comprise ablating an exterior of the atrial appendage with the electrode. In some instances, the method may further comprise cryoablating an exterior surface of the atrial appendage with the closure assembly.

In other variations, the methods described here may comprise positioning a distal end of a first guide element in the interior of an atrial appendage such as the left atrial appendage, positioning a distal end of a second guide element in a pericardial space externally of the atrial appendage, and advancing a closure assembly of a closure device around an exterior of the atrial appendage along the second guide. In some of these variations, the method may further comprise withdrawing the first guide element from the interior of the atrial appendage and closing the atrial appendage with the closure assembly. The method may further comprise advancing a portion of the first guide member into contact with tissue around the ostium of the closed atrial appendage, and ablating the contacted tissue with the first guide member.

In some of these methods, the first guide element and the second guide element may each comprise a magnet, and the method may further comprise aligning the first guide element and the second guide element across tissue of the atrial appendage. In some variations, the first guide element may comprise a balloon. In some of these variations, positioning the distal end of the first guide element may comprise positioning the balloon at least partially inside the atrial appendage. In some variations, the method may further comprise advancing a balloon catheter along the first guide element to position a balloon at least partially inside the left atrial appendage. In some of these variations, the balloon may comprise an electrode positioned on an exterior surface of the balloon, and the method may further comprise ablating interior tissue of the atrial appendage using the electrodes. In some variations, the balloon may comprise at least two electrodes and the method may further comprise monitoring a tissue parameter with at least one of the electrodes during ablation of the interior tissue. In some instances, the method may further comprise cryoablating interior tissue of the atrial appendage using the balloon or ablating interior tissue of the atrial appendage using the balloon while the balloon contains heated fluid.

In some of these methods, the first guide element comprises an electrode positioned at the distal end of the first guide element. Additionally or alternatively, the method may further comprise advancing a wire from a distal end of the first guide element, wherein advancing a portion of the first guide member into contact with tissue around the ostium of the closed atrial appendage comprises advancing the wire into contact with the tissue around the ostium of the closed atrial appendage. In some of these variations, the wire may be a j-tip wire or a coiled wire. In some instances, the method may further comprise cryoablating the tissue around the ostium with the wire. In some variations, the closure assembly may comprise one or more electrodes, and the method may further comprise ablating an exterior of the atrial appendage with the one or more electrodes. In other variations, the method may further comprise cryoablating an exterior surface of the atrial appendage with the closure device.

In still other variations of the methods described here, the methods may comprise advancing a distal end of a first device in the interior of an atrial appendage such as the left atrial appendage, wherein the first device comprises a shaft, a balloon, and an electrode or abrading element positioned on the shaft proximally of the balloon, and positioning the balloon in the atrial appendage. The method may further comprise advancing a closure assembly of a closure device around an exterior atrial appendage, partially closing the closure assembly to place interior tissue of the atrial appendage into contact with the electrode or abrading element, and ablating or abrading the interior tissue of the atrial appendage with the electrode or abrading element. In some variations, the method may further comprise removing the first device from the atrial appendage; and closing the atrial appendage with the closure assembly. In some of these methods, the first device may comprise two or more electrodes and the method may further comprise monitoring a tissue parameter with at least one of the electrodes during ablation of the interior tissue. In some variations, the closure assembly may comprise an electrode, and the method may further comprise ablating an exterior of the atrial appendage with the electrode.

In yet other variations of the methods described here, the methods may comprise positioning a closure assembly of a closure device around an exterior of the atrial appendage, wherein the closure assembly comprises a snare, a suture loop, a retention member releasably connecting the suture loop and the snare, and an electrode on the snare between a fixed end of the snare and the retention member, closing the closure assembly to close the atrial appendage, ablating exterior tissue of the atrial appendage with the electrodes, and releasing a suture loop from the closure assembly to hold the atrial appendage closed.

Also described here are systems for closing an atrial appendage. In some variations, the systems may comprise a catheter that may be configured to be advanced endovascularly into the interior of a heart, and a closure device that may be configured to be advanced into a pericardial space. The catheter may comprise an expandable member at a distal end of the catheter and the expandable member may be configured to ablate and/or abrade tissue. In some of these systems, the expandable member may be a balloon. The closure device may comprise a lumen therethrough, a handle, and a snare loop assembly. The snare loop assembly may extend from a distal end of the elongate body and may comprise a snare, a suture loop, and a retention member that may be configured to releasably couple the snare and the suture loop. In some variations, the snare may further comprise an electrode between a fixed end of the snare and the retention member, and the electrode may be configured to ablate an exterior of the atrial appendage. In yet other variations, the snare may be configured to cryoablate an exterior of the atrial appendage.

In some variations, the system may further comprise a first guide element that may be configured to be advanced into the interior of the atrial appendage, and a second guide element that may be configured to be advanced into a pericardial space. In some instances, the second guide element may be slideably disposed within the lumen of the closure device to advance the closure device into the pericardial space. In some variations, the catheter may be part of the first guide element. In some systems, the catheter may comprise a lumen therethrough and the first guide element may be slideably disposed within the lumen of the catheter to advance the catheter into the interior of the heart.

In some systems, the expandable member may comprise at least one electrode positioned on an exterior surface of the expandable member and the expandable member may be configured to ablate interior tissue with the at least one electrode. In some instances, the expandable member may comprise a balloon and the at least one electrode may circumferentially surround the exterior surface of the balloon. In some of these systems, one electrode may circumferentially surround the exterior surface of the balloon. In other systems, the expandable member may comprise at least two electrodes and at least one electrode may be configured to monitor at least one tissue parameter during ablation of the interior tissue. In these systems, the at least one tissue parameter may comprise at least one of: temperature, ECG signals, and/or the absence of ECG signals. In some variations, the expandable member may be inflated with cryogenic fluid and may be configured to cryoablate interior tissue. In yet other variations, the catheter may further comprise a shaft on which the expandable member is mounted, the shaft may comprise at least one electrode within the expandable member, and the expandable member may be configured to ablate interior tissue with fluid heated by the at least one electrode.

In some variations of the systems described here, the system may comprise a first guide element that may be configured to be advanced into the interior of the atrial appendage, a second guide that may be configured to be advanced into a pericardial space, and a closure device that may be configured to be advanced into a pericardial space. The first guide element may comprise a shaft and an expandable member, and the shaft may comprise an ablating and/or abrading element positioned proximally of the expandable member. In some of these systems, the, expandable member may be a balloon. The closure device may comprise an elongate body that may comprise a lumen therethrough, a handle, and a snare loop assembly. The snare loop assembly may extend from a distal end of the elongate body and may comprise a snare, a suture loop, and a retention member that may be configured to releasably couple the snare and the suture loop.

In some variations, the first and second guide elements may each comprise a magnet and may be configured to align across tissue of the atrial appendage. In some instances, the second guide element may be slideably disposed within the lumen of the closure device to advance the closure device into the pericardial space. Additionally or alternatively, the ablating and/or abrading element may be an electrode and the first guide may be configured to ablate interior tissue of the atrial appendage with the electrode. In some systems, the interior tissue of the atrial appendage may be tissue around an ostium of the atrial appendage. In some variations, the ablating and/or abrading element may comprise at least two electrodes and at least one electrode may be configured to monitor at least one tissue parameter during ablation of the interior'tissue. In some of these variations, the at least one tissue parameter may comprise: temperature, ECG signals, and/or the absence of ECG signals. In some instances, the snare may further comprise an electrode between a fixed end of the snare and the retention member, and the electrode may be configured to ablate an exterior of the atrial appendage. In yet other instances, the snare may be configured to cryoablate exterior surface of the atrial appendage.

In yet other variations of the systems described here, the system may comprise a first guide element that may be configured to be advanced into the interior of the atrial appendage, a second guide element that may be configured to be advanced into a pericardial space, a closure device that may be configured to be advanced into a pericardial space, and an ablating or abrading element that may be configured to ablate or abrade interior tissue of an atrial appendage. In some instances, the ablating or abrading element may comprise a j-tip, coiled, or ball-tipped wire. In some variations, the ablating or abrading element may be configured to cryoablate interior tissue of an atrial appendage.

The first guide element may comprise a proximal end, a distal end, a lumen therethrough, and a magnet on the distal end. The second guide element may comprise a proximal end, a distal end, and a magnet on the distal that may be configured to align the second guide element with the first guide element across tissue. In some variations, the first guide element may further comprise an expandable member and in some instances, the expandable member may be a balloon. The ablating or abrading element may be configured to be slideably disposed within a lumen of the first guide element and may be advanced from a distal end thereof. The second guide element may also be configured to be slideably disposed within a lumen of the closure device to advance the closure device into the pericardial space.

The closure device may comprise an elongate body that may comprise a lumen therethrough, a handle, and a snare loop assembly. The snare loop assembly may extend from a distal end of the elongate body and may comprise a snare, a suture loop, and a retention member that may be configured to releasably couple the snare and the suture loop. In some variations, the snare may further comprise an electrode between a fixed end of the snare and the retention member, and the electrode may be configured to ablate an exterior of the atrial appendage. In yet other variations, the snare may be configured to cryoablate an exterior of the atrial appendage.

BRIEF DESCRIPTION OF THE DRAWINGS

FIGS. 14A-14F depict variations of expandable members suitable for use with the systems described here.

FIGS. 15A and 15B depict cross-sectional side views of a variation of an expandable member catheter as described here.

DETAILED DESCRIPTION

Described here are systems and methods for closing the left atrial appendage. Generally, the systems and methods are configured to ablate or abrade left atrial appendage tissue before, during, or after the left atrial appendage closure procedure. In some instances, the left atrial appendage tissue may be ablated to electrically isolate the left atrial appendage from the heart. For example, for patients suffering from atrial fibrillation, electrical isolation of the left atrial appendage may limit the ability for asynchronous heart signals generated in the left atrial appendage to reach surrounding heart tissue. Additionally or alternatively, ablation or abrasion of left atrial appendage tissue may induce an inflammatory response from the left atrial appendage tissue, which may result in healing that may result in tissue fusion or otherwise help maintain closure of the left atrial appendage.

Figure 4:
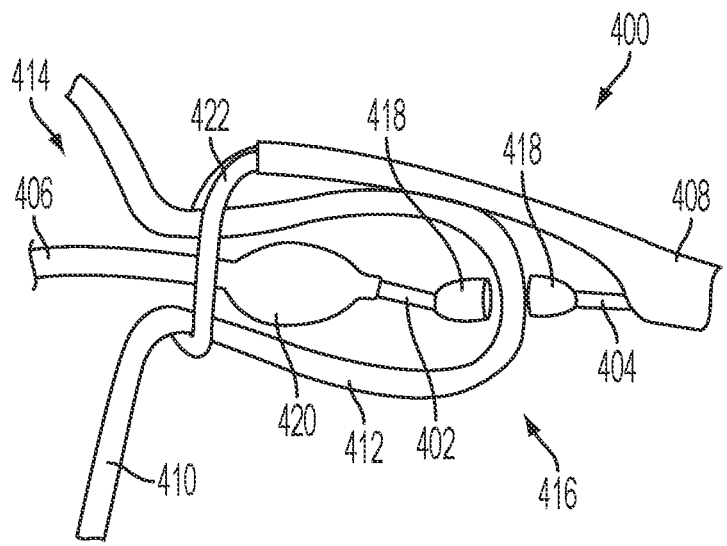
FIG. 4 depicts an illustrative variation of a system for closing the left atrial appendage.

Generally, the left atrial appendage may be closed using one or more of the systems described in U.S. patent application Ser. No. 13/490,919, filed on Jun. 7, 2012 and titled "TISSUE LIGATION DEVICES AND TENSIONING DEVICES THEREFOR," the content of which is hereby incorporated by reference in its entirety. FIG. 4 shows an illustrative variation of a closure system (400) that may be used to close the left atrial appendage. As shown there, the system may comprise a first guide element (402), a second guide element (404), an expandable member catheter (406), depicted here as a balloon catheter, and a closure device (408). Generally, the first and second guide elements may be configured to be positioned in the body and to act as guides for the advancement of devices in the body. For example, as shown in FIG. 4, a distal portion of the first guide element (402) may be introduced into the vasculature (e.g., via a femoral access site, brachial access site, or the like) and advanced into a heart (410) of a patient. In some instances, the first guide element (402) may be advanced to position a distal end of the first guide element (402) in the left atrial appendage (412). A proximal portion of the first guide element (402) may remain outside of the body such that one or more devices may be advanced along the first guide element (402) and into the body (e.g., the first guide element (402) may be slideably disposed within a lumen of a device such that the device may travel along the first guide element (402)). The device may be advanced along the first guide element (402) to position a distal portion of the device in the left atrium (414) or the left atrial appendage (412).

Similarly, a distal portion of the second guide element (404) may be positioned externally of the heart (410). For example, the second guide element (404) may be introduced into the body through an access point (e.g., intercostal access via a sternotomy, thoracostomy, or thoracotomy, right of the xiphoid process and pointed towards the patient's left shoulder, or in the costal cartilage or xiphoid process itself) and advanced to position a distal end of the second guide element into the pericardial space (416). A proximal portion of the second guide element (404) may remain outside of the body such that one or more devices may be advanced along the second guide element (404) to position a distal portion of the device in the pericardial space (416) (e.g., the second guide element (404) may be slideably disposed within a lumen of the device such that the device may travel along the second guide element (404)).

In some variations, the first guide element (402) and the second guide element (404) may be configured to align themselves across tissue of the heart. For example, in some variations, the first guide element (402) and the second guide element (404) may each comprise a magnet (418) at or near a distal end of the guide element. When the first guide element (402) and the second guide element (404) are positioned on opposite sides of heart tissue, the magnet (418) of the first guide element (402) may be attracted to the magnet (418) of the second guide element (404) (and vice versa), which may align the first and second guide elements. In some instances, as shown in FIG. 4, a distal end of the first guide element (402) may be positioned in the left atrial appendage (412), and a distal end of the second guide element (404) may be aligned with the first guide element (402) across tissue of the left atrial appendage (412) (e.g., via magnets). While shown in FIG. 4 as being aligned via magnets (418), the first guide element (402) and second guide element (404) may be manually aligned (e.g., via manipulation of the first and second guide elements under visualization such as fluoroscopy). It should also be appreciated that first and/or second guide elements may be any member suitable for advancement through the vasculature or the pericardial space, such as, for example, a catheter, wire, hollow wire, or the like.

The expandable member catheter (406) is generally configured to be advanced for endovascularly into the heart (410). For example, in some variations, the expandable member catheter (406) may be configured to be advanced along the first guide element (402) (e.g., in an over-the-wire configuration, a rapid-exchange configuration, or the like) to position a distal portion of the expandable member catheter (406) in the heart (410) (e.g., in the left atrium (414), the left atrial appendage (412) or the like). The expandable member catheter (406) may compose an expandable member, for example, an inflatable balloon (420) or other expandable structure. The balloon (420) or expandable member may be positioned at least partially inside of the left atrial appendage (412), and may be expanded. When expanded, the balloon (420) or expandable member may press against or otherwise support a portion of the left atrial appendage (412). Additionally or alternatively, the balloon (420) or expandable member may be filled or coated with a contrast material, which may assist in visualization of the left atrial appendage (412) during the closure procedure. When the expandable member catheter (406) is positioned along a portion of the first guide element (402), the expandable member catheter (406) may be advanced over the first guide element (402) after the first guide element (402) has been positioned, or may be positioned simultaneously with the first guide element (402). In other variations, the system (400) may not comprise an expandable member catheter (406) separate from first guide element (402). In some of these variations, the first guide element (402) may comprise an inflatable balloon (420) or an expandable member, which may be expanded (e.g., in the left atrial appendage (412) as discussed above). In other variations, the system (400) may not include an expandable member positioned in the left atrial appendage (412).

The closure device (408) is generally configured to close the left atrial appendage. The closure device (408) may be advanced along the second guide element (404) to position a distal portion of the closure device (408) in the pericardial space (416). Advancement of the closure device (408) into the pericardial space (416) may also position a closure assembly (422) (such as a snare loop assembly, as will be discussed in more detail below) around an external portion of the left atrial appendage (412). The closure assembly (422) may be actuated to close the closure assembly (422) around the left atrial appendage (412), which may at least partially close the left atrial appendage (412). In some instances, the closure assembly (422) may be at least partially reopened to allow the left atrial appendage (412) to at least partially reopen and/or to remove the closure assembly (422). In some variations, the closure assembly (422) may be configured to release a suture loop or other deployable loop which may hold the left atrial appendage (412) in a closed configuration.

Figure 3:
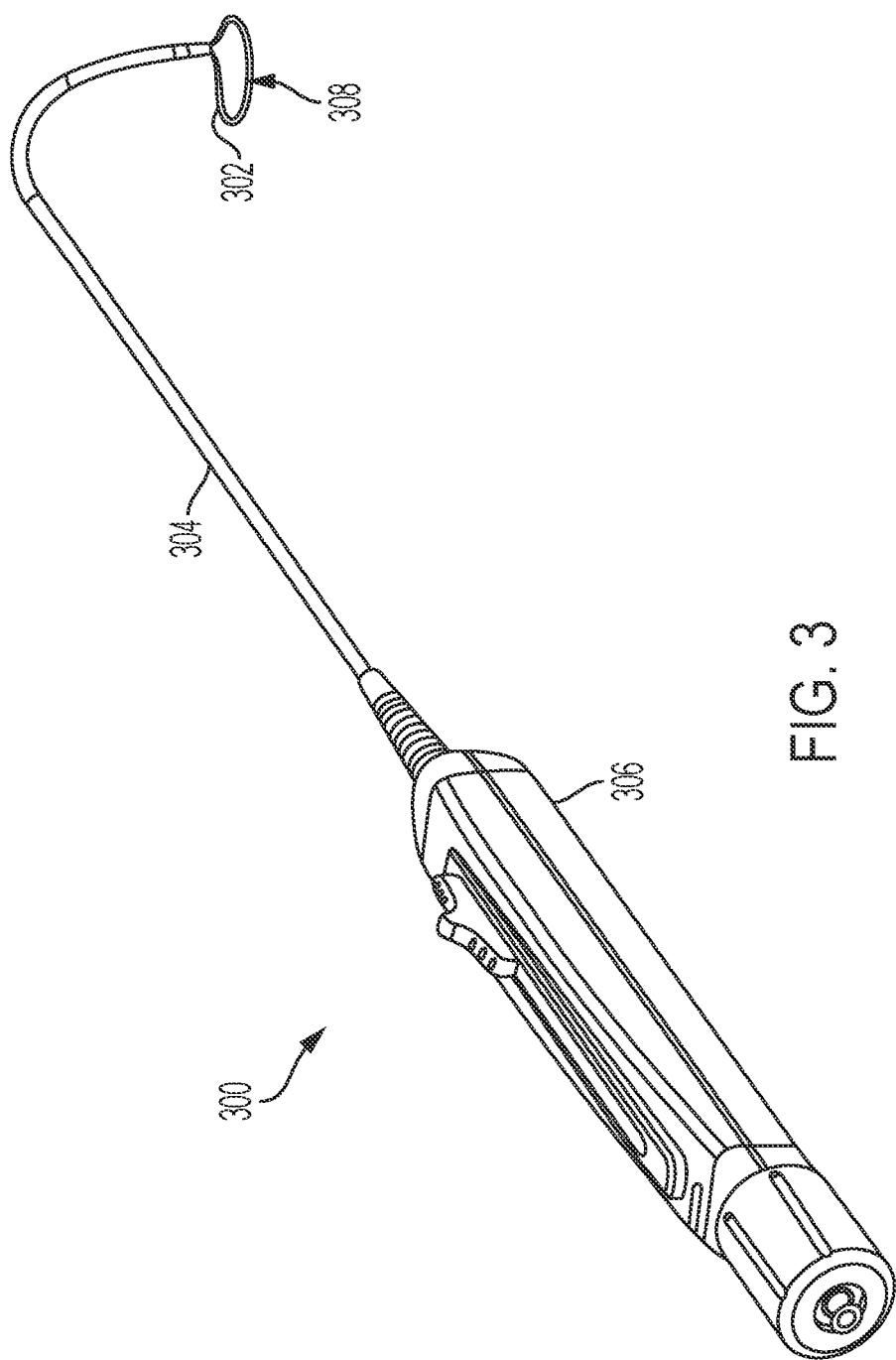
FIG. 3 is a perspective view of an illustrative closure device as described here.

FIG. 3 depicts one illustrative variation of a closure device (300) as described here. As shown there, the closure device (300) may comprise a snare loop assembly (302), an elongate body (304), and a handle (306). Generally, a portion of the snare loop assembly (302) extends from a distal portion of the elongate body (304) to form a continuous loop (308), which may allow the snare loop assembly (302) and the elongate body (304) to encircle tissue placed in the loop (308). The handle (306) may be used to control and actuate the snare loop assembly (302) through the elongate body (304) in order to increase or decrease the size of the loop (308) (e.g., increase or decrease the loop's circumference or diameter). For example, the handle (306) may advance a portion of the snare loop assembly (302) out of the elongate body (304) to increase the size of the loop (308), or may withdraw a portion of the snare loop assembly (302) into the elongate body (304) to decrease the size of the loop (308). Accordingly, the size of the loop (308) may be increased to allow the snare loop assembly (302) to be placed around tissue. Once around tissue, the size of the loop (308) may be decreased to ligate/close tissue (e.g., such as the left atrial appendage, as discussed above with respect to FIG. 4). The size of the loop (308) may then be increased to allow the tissue to be at least partially unclosed and/or to disengage the snare loop assembly (302) from tissue.

Figure 1:
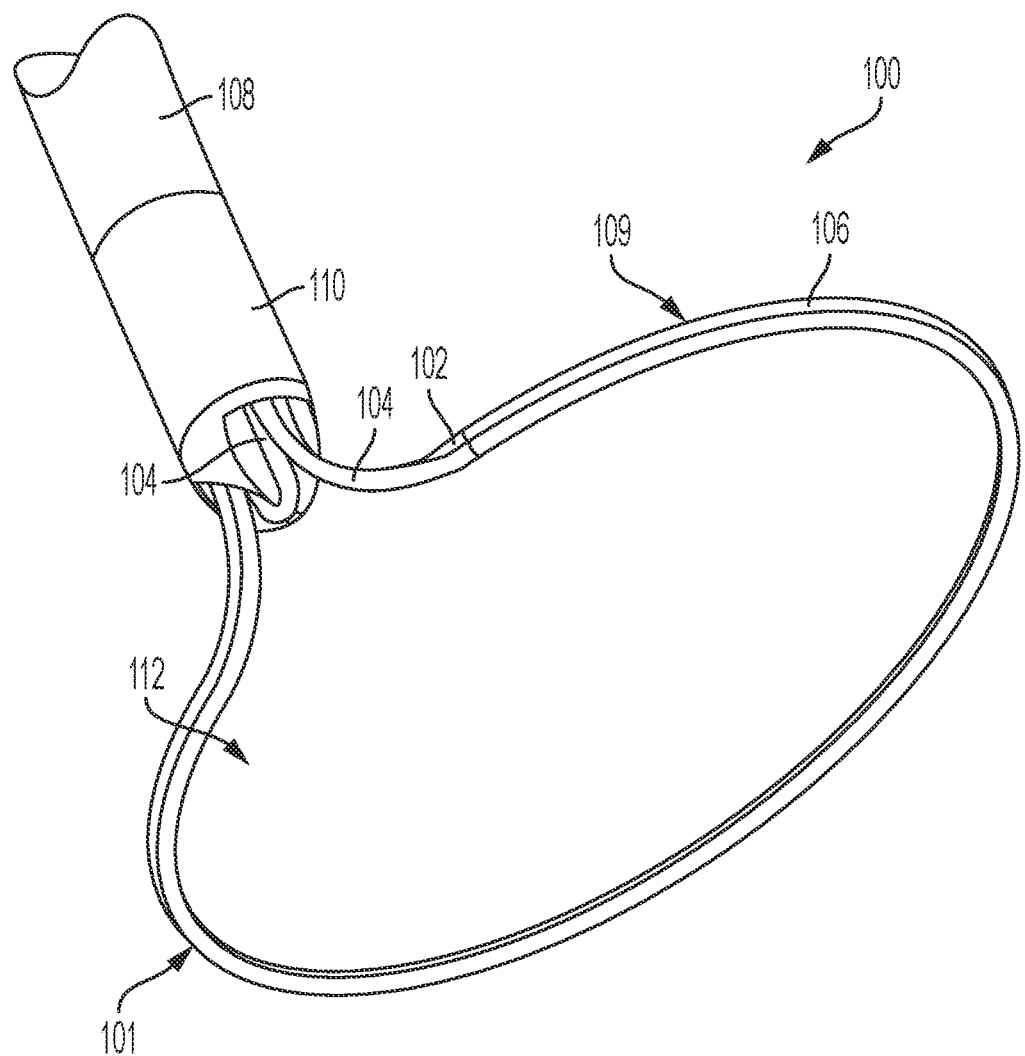
FIG. 1 depicts a distal end of an illustrative variation of a closure device having a snare loop assembly.

The snare loop assemblies of the closure devices described here generally comprise a snare and a suture loop releasably coupled thereto. For example, FIG. 1 shows a distal portion of an illustrative variation of a closure device (100) comprising a snare loop assembly (101) and an elongate body (108) having a tip (110). As shown there, the snare loop assembly (101) may comprise a snare (102), a suture loop (104), and a retention member (106), and may be disposed relative to the elongate body (108) such that at least a portion of the snare loop assembly (101) extends from the elongate body (108) (e.g., out of tip (110)). The snare loop assembly (101) is shown in FIG. 1 in an open configuration, and the portion of snare loop assembly (101) extending out of elongate body (104) may form a loop (109) having an aperture (112) therethrough, such as discussed above. The loop (109) and corresponding aperture (112) may be defined by one or more components of the snare loop assembly (101) (e.g., the snare), and may be suitable for encircling tissue such as the left atrial appendage.

Figure 2:
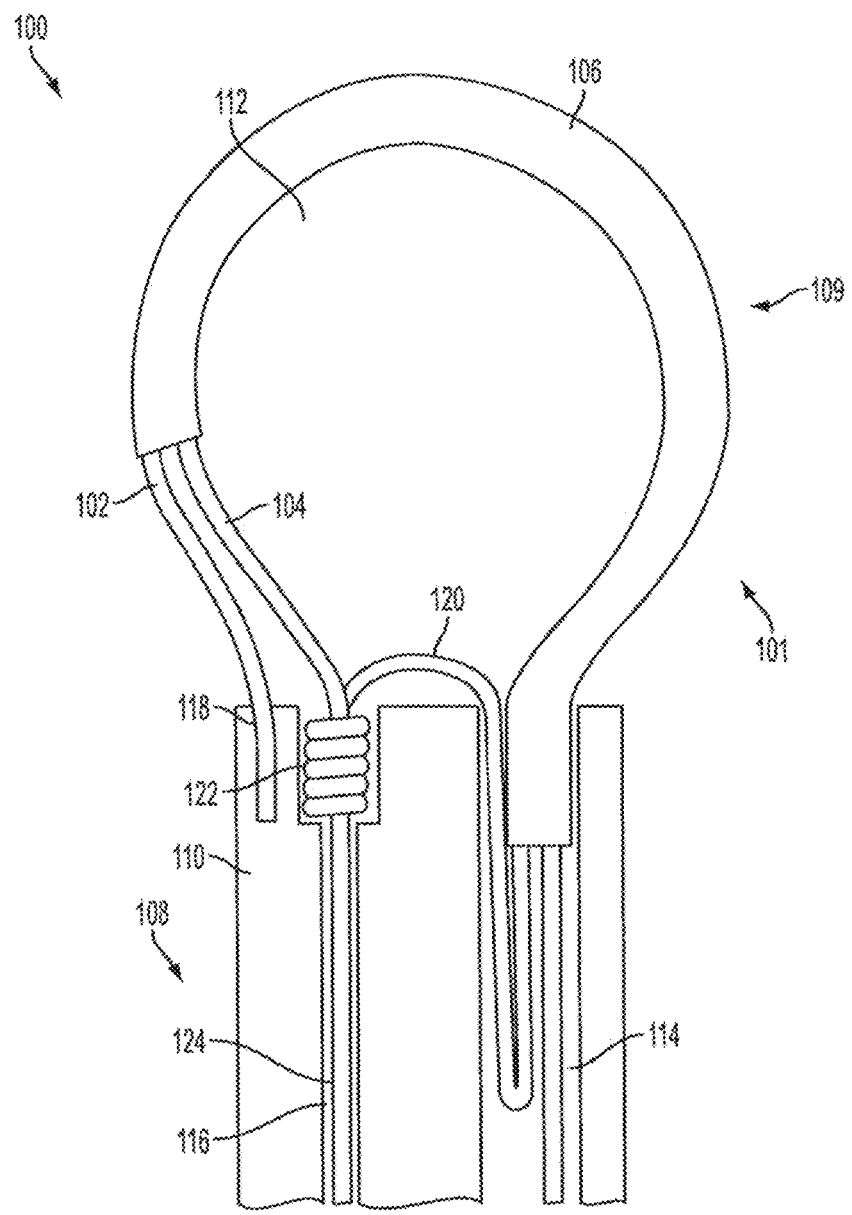
FIG. 2 shows a cross-sectional side view of the closure device of FIG. 1.

Generally, the snare (102) may be actuated (e.g., by a portion of a handle or other control portion of the closure device) to control the size of the loop (109) of the snare loop assembly (101). For example, FIG. 2 shows a cross-sectional side view of the closure device (100). As shown there, the elongate body (108) may comprise a first lumen (114) and a second lumen (116). One end (118) of the snare (102) may be fixedly attached to the elongate body (108) (e.g., attached to the tip (110)), while a second end (not shown) of the snare may pass through the first lumen (114), where it may be operatively attached to a snare control (not shown). The snare control may be configured to advance or retract the snare (102) relative to the elongate body (108), which may control the amount of the snare (102) (and with it, the snare loop assembly (101)) extending from the elongate body (108). This in turn may control the size (e.g., circumference or diameter) of the loop (109) of the snare loop assembly (101).

As mentioned above, a suture loop (104) may be releasably connected to the snare (102). For example, as shown in FIGS. 1 and 2, the suture loop (104) may be releasably coupled to the snare (102) via a retention member (106). The retention member (106) may be any suitable structure, such as a dual-lumen tube or one or more of the retention members described in U.S. patent application Ser. No. 13/490,919, which was previously incorporated by reference in its entirety. The suture loop (104) may be initially configured to have a diameter larger than that of the snare loop assembly (101) when the snare loop assembly (101) is opened (excess suture of the suture loop (104) may be housed in the elongate body (108), such as described in U.S. patent application Ser. No. 13/490,919, which was previously incorporated by reference in its entirety).

The suture loop (104) may be tightened to reduce the diameter of the suture loop (104). When the diameter of the suture loop (104) is reduced past the diameter of the loop (109) of the snare loop assembly (101), the suture loop (104) may disengage and be released from the snare loop assembly (101). For example, tightening the suture loop (104) may cause the suture loop (104) to pull or tear through one or more walls, slits, prongs, arms or the like of the retention member (106) to break the connection between the suture loop (104) and the retention member (106).

Generally, the suture loop (104) may comprise a loop portion (120), a suture knot (122) and a tail (124). As shown in FIG. 2, the suture knot (122) may be temporarily held at least partially within the tip (110) of the elongate body (108). The suture of the loop portion (120) may be pulled through the suture knot (122) to reduce the diameter of the loop portion (120). The suture tail may extend through the elongate body (108) through the second lumen (116) of the elongate body (108)), and may be operatively attached to a suture control (not shown). The suture control may be used to pull the suture tail (124), which in turn may reduce the diameter of the loop portion (120) of the suture loop. When the snare (102) is advanced or withdrawn relative to the first lumen (114) of the elongate body (108), a portion of the suture loop (104) and the retention member (106) may also be advanced out of or withdrawn into the first lumen (114) of the elongate body (108). The suture knot (120) is preferably a one-way knot (e.g., a slip-knot), which allows the suture loop to maintain its diameter as the suture loop (104) is tightened. Additionally or alternatively, the suture loop (104) may comprise one or more unidirectional locking structures (such as those described in U.S. patent application Ser. No. 13/490,919, which was previously incorporated by reference in its entirety) which may help prevent the loop portion (120) from increasing in diameter (e.g., in response to expansive forces provided by the ligated tissue) of the suture loop (104) after it is tightened.

To close a tissue (such as the left atrial appendage) with the closure device (100), the closure device (100) may be advanced to the target tissue. Generally, the closure devices described here may be suitable for use using minimally invasive access to the left atrial appendage (e.g., through a small incision above, beneath or through the rib cage, through an incision in the costal cartilage or the xiphoid, through a port, through the vasculature, etc.), as discussed above. The moveable end of the snare (102) may be advanced relative to the elongate body (108) to increase the diameter of the loop (109) of the snare loop assembly (101) to "open" the snare loop assembly. With the snare loop assembly in an open configuration, the loop (109) may be placed around the target tissue to encircle the tissue. The moveable end of the snare (102) may he withdrawn relative to the elongate body (108) to decrease the diameter of the loop (109), which may close the snare loop assembly (101) around the tissue. With the tissue held in a closed configuration by the snare (102) and the snare loop assembly (101), the suture loop (104) may be tightened (i.e., the diameter of the loop portion (120) may be reduced by pulling the tail (124) relative to the suture knot (122)) to release the suture loop (104) from the snare loop assembly (101). Once released, the suture loop (104) may hold the tissue in a ligated configuration, and the remaining portions of the closure device (100) may be removed. In some instances, the suture loop (104) may be further tightened to reduce the diameter of the suture loop (104), as will be discussed in more detail below.

As mentioned above, one or more portions of the closure systems described here may be configured to ablate or abrade left atrial appendage tissue during the closure procedures described generally above. Generally, left atrial appendage tissue may be ablated or abraded from an endocardial approach (i.e., from an interior of the heart), an epicardial approach (i.e., from an exterior of the heart), or a combination of endocardial and epicardial approaches. For the purposes of this application, "interior tissue" of the left atrial appendage or heart will refer to internal tissue surfaces of the left atrial appendage or heart, respectively, which are accessible from the interior of the, heart and/or left atrial appendage. Conversely, "exterior tissue" of the left atrial appendage or heart will refer to external tissue surfaces of the left atrial appendage or heart, respectively, which are accessible from an exterior of the heart and/or left atrial appendage.

Figure 5A:
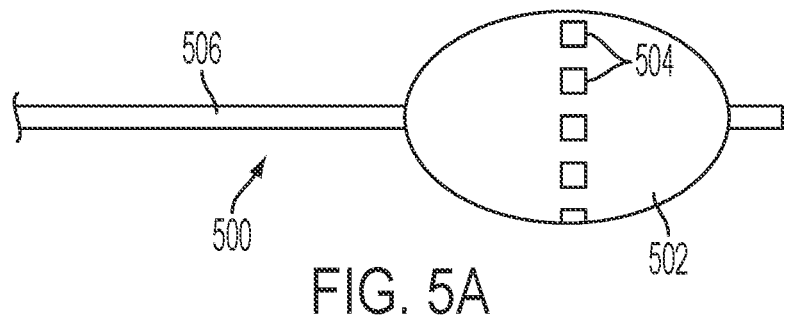
FIGS. 5A-5C depict side views of different variations of expandable member catheters suitable for use with the systems described here.
Figure 5B:
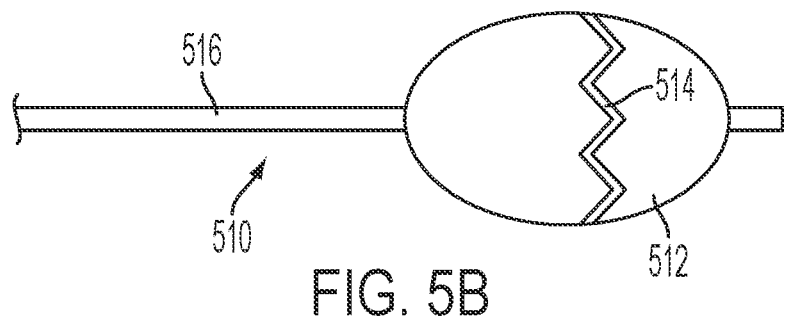
Figure 5C:
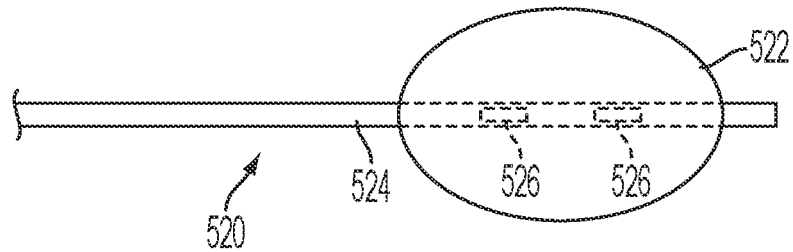

When the closure systems described here comprise an inflatable balloon or other expandable member (e.g., as part of an expandable member catheter or a first guide element), the expandable member may be configured to ablate or abrade tissue. FIGS. 5A-5C depict different variations of expandable member catheters in the form of balloon catheters configured to provide ablation energy to tissue. It should be appreciated that each of these variations may be incorporated into a guide element having an inflatable or expandable member. FIG. 5A shows a side view of a first variation of a balloon catheter (500) having an inflatable balloon (502) (although it should be appreciated that the balloon catheter (500) may comprise any suitable inflatable or expandable member). As shown there, the balloon (502) may comprise a plurality of abrading (e.g., a roughened surface, one or more barbs, spikes, hooks, or the like) or ablating (e.g., electrodes) elements (504) positioned around an exterior surface of the balloon (502). In variations used for ablation, the expansion of the balloon (502) may press one or more of the electrodes (504) against tissue, and energy may be delivered to tissue via one or more of the electrodes (504) to ablate tissue. The energy may be delivered from any suitable energy source, including but not limited to, a transducer to deliver high-intensity focused ultrasound to the tissue to locally heat and ablate it, a laser, an RF generator, etc. In some variations, one or more of the electrodes (504) may be configured to monitor one or more tissue parameters (e.g., temperature, ECG signals, the presence or absence of ECG signals) during ablation. The electrodes (504) may be electrically connected to a proximal portion of the balloon catheter (500) via one or more leads (not shown) incorporated into or on a shaft (506) of the balloon catheter (500).

In some variations, one or more of the electrodes of a balloon may be configured to circumferentially surround the balloon. For example, FIG. 5B shows another variation of a balloon catheter (510) having a balloon (512) or other expandable member. As shown there, the balloon catheter (510) may comprise at least one electrode (514) connected to the balloon (512). As shown there, the electrode (514) may be configured to circumferentially surround the balloon (512). In these variations, the electrode (514) may be flexible or otherwise configured to match the shape of the balloon (512) during inflation and deflation of the balloon (512). When the balloon (512) is expanded, the balloon (512) may press the electrode (514) into contact with tissue, and energy may be supplied to the tissue via the electrode (514) to ablate tissue. The circumferential nature of the electrode (514) may allow the electrode (514) to ablate a ring of tissue (e.g., when positioned inside of the left atrial appendage). While shown in FIG. 5B as having a single electrode (514), it should be appreciated that the balloon catheter (510) may comprise a plurality of electrodes attached to the balloon (512), such as described above. The electrodes (514) may be electrically connected to a proximal portion of the balloon catheter (510) via one or more leads (not shown) incorporate into or on a shaft (516) of the balloon catheter (510).

In other variations, the balloon catheter may be configured to thermally ablate tissue. For example, FIG. 5C shows another variation of a balloon catheter (520) having a balloon (522). As shown there, the balloon (522) may be mounted to a shaft (524), and the balloon catheter (520) may include one or more electrodes (526) mounted on the shaft (524) within the balloon (522). In these variations, fluid (e.g., saline, a saline/contrast fluid mixture) may be introduced into the balloon (522) (e.g., through an inflation port (not shown) on the shaft inside the balloon (522)) to inflate the balloon (522). RF energy may be supplied to the one or more electrodes (526), which may heat the one or more electrodes (526) and the fluid in the balloon (522). In some variations, the shaft inside of the balloon (522) may comprise one or more resistive heating elements connected to an electrical source, which may heat the fluid inside of the balloon. As the fluid in the balloon is heated, tissue in contact with the balloon may he heated to ablate the tissue. In other variations, the balloon catheter may be configured to introduce a cooled fluid into the balloon (522), which may cryoablate tissue in contact with the balloon (522). In yet other variations, the balloon catheter may be configured to introduce or apply therapeutic compounds (e.g., to promote healing) to the tissue. For example, in some instances the balloon (522) may comprise one or more porous materials such that the balloon catheter may also be used for drug delivery.

Figure 14E:
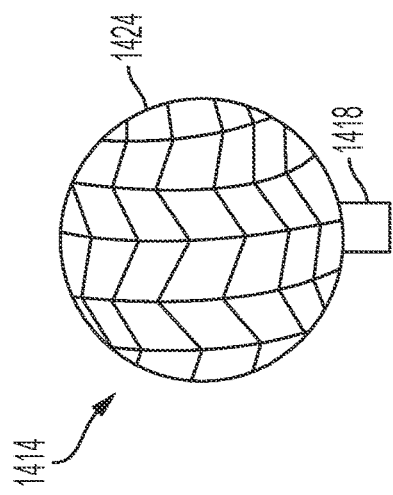

In some variations, the expandable member may comprise a loop or a metal form similar to a stent or an interior vena cava filter. For example, FIGS. 14A-14F depict embodiments of expandable members for ablating or abrading the interior tissue of the LAA. FIGS. 14A and 14B illustrate an expandable member catheter comprising an expandable member (1414) in the form of an actuatable electrode or abrading loop (1402) that may be advanced from a distal end of an elongate body (1406). The loop (1402) may be actuated (e.g., by an actuator (not pictured) on a handle or other control portion of the catheter) to control the size of loop (1402) (e.g., diameter and/or circumference) and the location of ablation or abrading. As can be seen in FIGS. 14A and 14B, the elongate body (1406) may comprise a lumen (1408) through which the distal end (1410) of the loop (1402) travels to connect to the actuator. The proximal end (1404) of the loop (1402) may be fixed to the elongate body (1406). The actuator may be configured to advance or retract the distal end (1410) of the loop (1402) relative to the elongate body (1406) to control the amount of the loop (1402) extending from the elongate body (1406) and thus the size (e.g., circumference and/or diameter) of the loop (1402).

The loop (1402) may comprise a conductive material such that the loop (1402) functions as an electrode to ablate tissue when connected to an energy source and energized. The loop (1402) may comprise a protective coating or sleeve which may help prevent inadvertent ablation when the loop (1402) is energized but not yet properly placed. In some embodiments, the loop (1402) may comprise ablating or abrading elements (1412), as depicted in FIG. 14B. In some variations, the ablating or abrading elements (1412) may comprise electrodes (e.g., RF electrodes). Additionally or alternatively, the ablating or abrading elements (1412) may comprise a roughened surface, one or more barbs, spikes, hooks, or the like. In variations in which the loop (1402) itself may be energized, the loop (1402) may also comprise abrading elements (1412). In other variations, the loop (1402) may comprise a lumen therethrough and may be connected at its distal end to a fluid source. The cryogenic fluid may flow through the loop's (1402) lumen such that the loop (1402) may be used to cryoablate the interior tissue of the LAA. In some embodiments, the loop may further comprise apertures such that the loop (1402) may deliver or dispense a therapeutic compound or an adhesive to the internal surface of the LAA, which may assist with tissue healing and/or LAA closure.

Figure 14F:
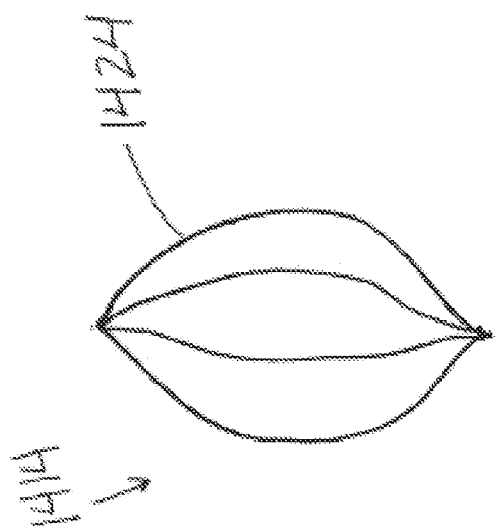
Figure 14C:
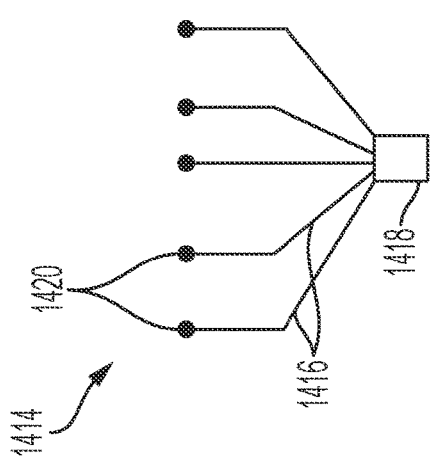
Figure 14D:
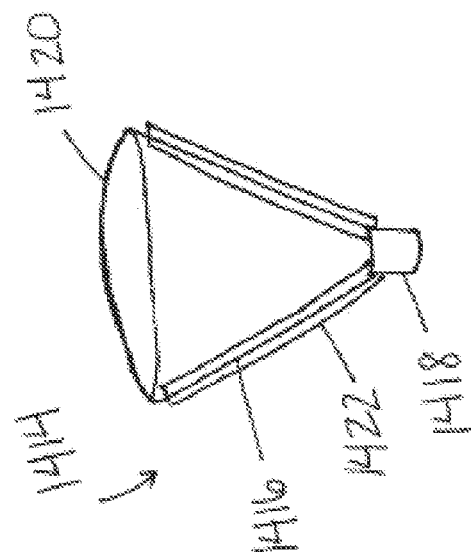

FIGS. 14D-14F depict additional embodiments of expandable members (1414) that may be utilized with the expandable member catheter. FIG. 14C depicts an expandable member comprising a plurality of arms (1416) extending distally from a central hub (1418). In some embodiments, the arms (1416) may extend outward such that their distal tips form a circle, oval, hexagon, octagon, or any other desired shape. As depicted there, each arm (1416) comprises an ablating or abrading element (1420) at its distal tip, but the arms may comprise ablating or abrading elements (1420) at any location along their lengths. Moreover, every arm (1416) need not comprise an ablating or abrading element (1420), and any number of ablating or abrading elements may be utilized. In some variations, the arms (1420) may be made of a conductive material and connected to an energy source such that the arms themselves may ablate tissue. In other variations, the expandable member (1414) may be made of a rigid polymer and may comprise abrading or ablating elements strategically placed on the expandable member (1414) based on the user's desired ablation locations. FIG. 14D depicts another variation of an expandable member (1414) comprising two arms (1416) supporting a circular ablating or abrading element (1420). The arms (1416) comprise protective coverings (1422) (e.g., a sleeve, polymer coating, etc.) which may protect the tissue when the arms (1416) also comprise abrading or ablating elements, or may otherwise damage tissue undesirably. FIGS. 14E and 14F depict variations of the expandable members (1414) comprising wire form or stent-like configurations and which comprise rounded bodies (1424) (e.g., comprising circular, oval, etc. cross-sections) in their expanded configurations. These expandable members (1414) may comprise any number of abrading or ablating elements, and/or may themselves be ablating or abrading elements (e.g., the wires that form the bodies (1424) may ablate or abrade tissue).

The expandable members may comprise a first retracted position and a second expanded position and may be constructed of a resilient material (e.g., a shape-memory material like nitinol) such that the expandable members may be advanced to the LAA in the retracted position (for example, as shown in FIG. 15A) and may be subsequently advanced into the expanded position (e.g., as shown in FIG. 15B) once proper placement is achieved. In the variation shown in FIGS. 15A and 15B, the expandable member (1514) is slideably disposed within the lumen (1508) of the catheter's elongate body (1506). The hub (1518) is connected to a second elongate body (1502) such that a user may advance the expandable member (1514) distally relative to the catheter's elongate body (1506) to move the expandable member from its retracted position (in which it is constrained) to its expanded position (in which it is no longer constrained). In some variations, the expandable member (1514) may comprise a hub (1518) at the proximal and distal ends of its arms or body. In these embodiments, the expandable member catheter may be configured such that the hub at the distal end of the expandable member catheter may be fixed and the hub at the proximal end may slide distally such that the hubs at the proximal and distal ends of the expandable member move toward each other to move the expandable member from its retracted position to its expanded position. In some variations, the expandable member (1514) may be coupled to the expandable member catheter but not disposed within its lumen.

In some embodiments, the systems described here may comprise two expandable member catheters. For example, the system may comprise a first expandable member catheter comprising a balloon (i.e., a balloon catheter) and a second expandable member catheter comprising any of the expandable members (1414) previously described (e.g., those depicted in FIGS. 14A-14F.) In these systems, a user may advance the balloon catheter into the LAA for use with the closure device, as described in detail below, and may remove the balloon catheter once the snare loop assembly has been deployed. The second expandable member catheter may then be advanced to the interior of the LAA specifically for the purpose of abrading or ablating tissue.

Figure 6A:
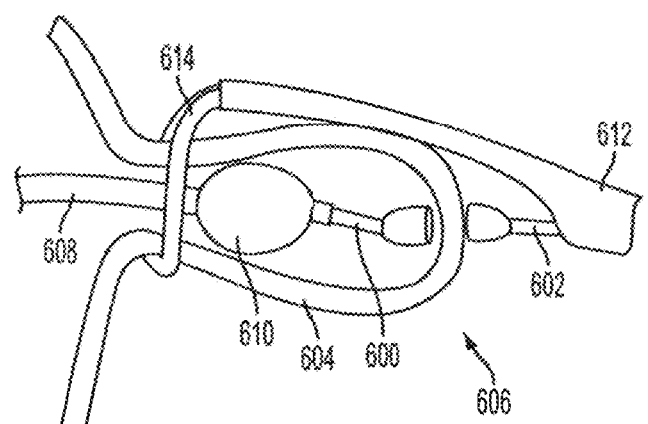
FIGS. 6A-6C depict an illustrative method of closing the left atrial appendage as discussed here.
Figure 6B:
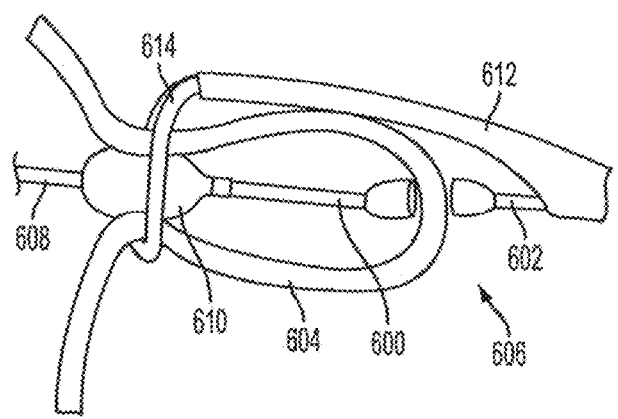
Figure 6C:
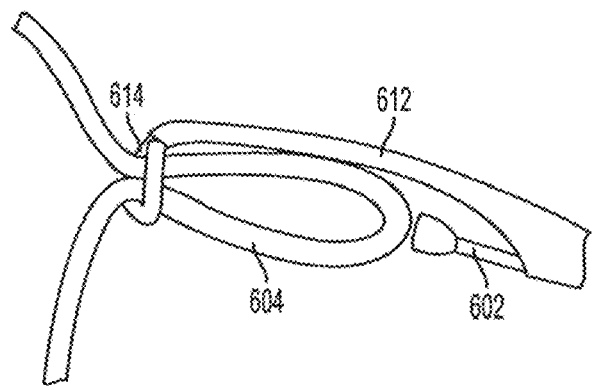

Any of the balloons described above may be used to ablate an interior tissue of the left atrial appendage. FIGS. 6A-6C depict an illustrative method by which a balloon may be used to ablate interior tissue of the left atrial appendage. As shown in FIG. 6A, a first guide element (600) and a second guide element (602) may be advanced and positioned such that a distal end of the first guide element (600) is positioned in the left atrial appendage (604) and a distal end of the second guide element (602) is positioned outside the left atrial appendage (604) in the pericardial space (606). The first guide element (600) and second guide element (602) may be aligned (e.g., using one or more magnets (not shown), such as described in more detail above with respect to FIG. 4). In some variations, a balloon catheter (608) may be advanced to position a balloon (610) in the left atrial appendage (604). In some of these variations, the balloon catheter (608) may be advanced along the first guide (600) after the first guide element (600) has been positioned in the left atrial appendage (604). In other variations, the balloon catheter (608) may be advanced simultarpeously with the first guide element (600). In still other variations, the system may not comprise a balloon catheter (608), but instead the balloon (610) may be part of the first guide element (600), such that advancement of the first guide element (600) into the left atrial appendage (604) positions the balloon (610) in the left atrial appendage (604). The balloon (610) may then be inflated inside of the left atrial appendage (604).

Additionally, a closure device (612) may be advanced along the second guide element (602) to position a closure assembly (614) (such as a snare loop assemblies as discussed above with respect to FIGS. 1-3) around the left atrial appendage. With the balloon (610) positioned in the left atrial appendage (604) and the closure assembly (614) positioned around the left atrial appendage (604), the closure assembly (614) may be at least partially dosed to close the left atrial appendage (604) around the balloon (610). In some variations, prior to closing the closure assembly (614), the balloon (610) and the closure assembly (614) may be positioned such that the balloon (610) is positioned inside of the closure assembly (614).

In other variations, the balloon (610) and closure assembly (614) may be initially positioned such that the closure assembly (614) is advanced past the balloon (610) and is positioned around a portion of the balloon catheter (608) (or the first guide element (600) in variations where the balloon (610) is part of the first guide element (600)) proximal of the balloon (610), such as shown in FIG. 6A. In these variations, the closure assembly (614) may be partially closed around the left atrial appendage (604) with the balloon (610) inflated to partially grab the left atrial appendage (604). With the closure assembly (614) engaging the left atrial appendage, the balloon (610) may be deflated and retracted (by retracting the balloon catheter (608), or the first guide element (600) in variations where the balloon (610) is part of the first guide element (600)) to position the balloon (610) inside of the closure assembly (614). The balloon (610) may be re-inflated to press the balloon (610) in contact with the interior tissue of the left atrial appendage (604), such as shown in FIG. 6B. In some of these variations, the closure assembly (614) may also be further closed to further pull tissue of the left atrial appendage (604).

With the left atrial appendage (604) closed around the balloon (610), the balloon (610) may be used to ablate or abrade the interior tissue that is captured by the closure assembly (614). This ablation or abrading may be done in any suitable manner. In variations where the balloon (610) comprises one or more electrodes (such as the electrodes (504) of the balloon (502) described above with respect to FIG. 5A or the electrode (514) of the balloon (512) described above with respect to FIG. 5B), the left atrial appendage (604) may be closed around the balloon (610) to press the interior tissue of the left atrial appendage in contact with some or all of the electrodes. RF energy may be supplied to the electrodes (514) to ablate the interior tissue. In variations where the balloon (610) includes one or more electrodes positioned within the balloon (such as the balloon (522) described above with respect to FIG. 5C), the electrodes may be used to heat a fluid in the balloon (610) such that the heat is transferred from the balloon to the interior tissue of the left atrial appendage (604) that is in contact with the balloon (610) to ablate tissue. In variations in which a cooled fluid is introduced into the balloon, the balloon may be used to cryoablate the interior tissue of the left atrial appendage (604) that is in contact with the balloon (610). In variations in which the balloon comprises abrading elements, the abrading elements may be used to physically damage or abrade tissue when moved against the tissue. In variations in which the balloon comprises porous materials, the balloon may be used to locally deliver therapeutic compounds to the surrounding tissue.

Following tissue ablation, the balloon (610) may be deflated and removed from the left atrial appendage (e.g., the first guide element (600) may be removed from the left atrial appendage, as well as the balloon catheter (608) in variations where the balloon (610) is part of the balloon catheter (608)). The closure assembly (614) may then be further closed to fully close the left atrial appendage (604), such as shown in FIG. 6C. In some variations, a suture loop or similar device may be deployed from the closure assembly (614) to maintain the left atrial appendage (604) in a closed configuration.

Figure 7A:
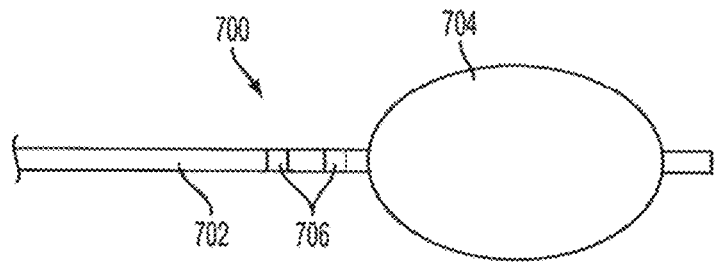
FIGS. 7A-7D depict side views of illustrative variations of devices suitable for use with the systems described here.

In other variations, one or more portions of the shaft of a balloon catheter or guide element may be used to ablate or abrade tissue. FIG. 7A shows one such variation of a balloon catheter (700) as described here. As shown there, the balloon catheter (700) may comprise a shaft (702), a balloon (704), and one or more electrodes or abrading elements (706) positioned on the shaft (702) proximally of the balloon (704). While shown in FIG. 7A as having a plurality of electrodes or abrading elements (706), in some variations the balloon catheter (700) may only comprise a single electrode or abrading element (706). In some variations, a balloon catheter may comprise at least one electrode and at least one abrading element positioned on a shaft of the balloon catheter proximal to the balloon. In some variations, elements (706) may comprise magnets, electromagnets, or magnetic material which may help with proper placement of the closure device, and more specifically, the snare loop assembly of the closure device, in embodiments in which the closure device comprises magnetic material. Elements (706) may be any combination of ablating, abrading, and magnetic elements. As discussed above, the ablating or abrading elements need not necessarily be incorporated on the balloon catheter and could instead be on a separate device that is advanced into the LAA after the balloon catheter is removed, but before the suture loop is deployed.

Figure 7B:
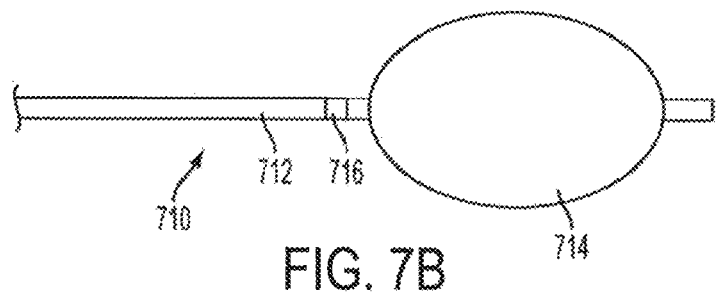

As mentioned above, the balloon catheter may comprise one or more abrading elements positioned on the shaft of the balloon catheter. For example, FIG. 7B shows one such variation of a balloon catheter (710), where the balloon catheter (710) may comprise a shaft (712), a balloon (714), and an abrading element (716) positioned on the shaft (712) proximal to the balloon (714). The abrading element (716) is generally configured such that it may physically damage or abrade tissue when moved against the tissue, as will be discussed in more detail below. For example, the abrading element (716) may include a roughened surface, one or more barbs, spikes, hooks, or the like.

Figure 7C:
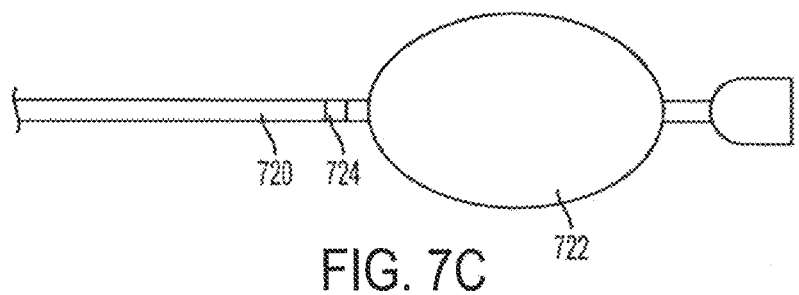
Figure 7D:
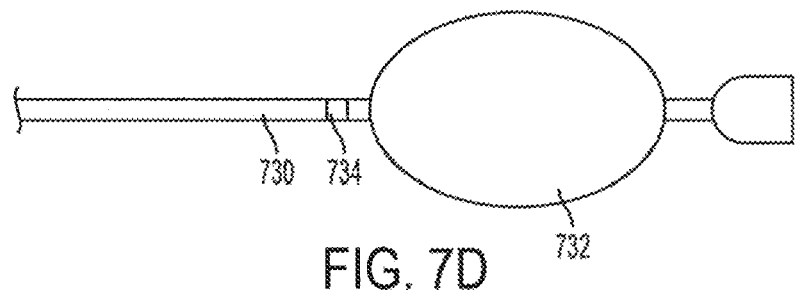

In variations where a guide element comprises a balloon (e.g., in place of having a separate balloon catheter), the guide element may comprise one or more electrodes and/or abrading elements positioned on the guide element proximally of the balloon. For example, FIG. 7C shows a variation of guide element (720) having a balloon (722) and one or more electrodes (724) positioned on the guide element (720) proximally of the balloon (722). FIG. 7D shows another variation of a guide element (730) having a balloon (732) and one or more abrading elements (734) positioned on the guide element (730) proximally of the balloon (732). In these variations, the guide element may comprise any number and combination of electrodes and or ablation elements, such as described above.

Figure 8A:
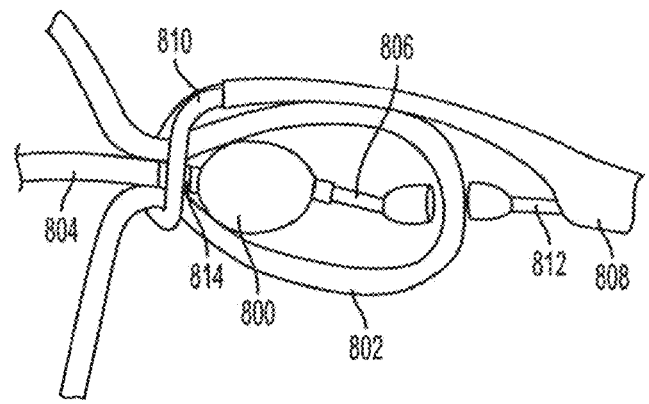
FIGS. 8A and 8B depict an illustrative method of closing the left atrial appendage as described here.
Figure 8B:
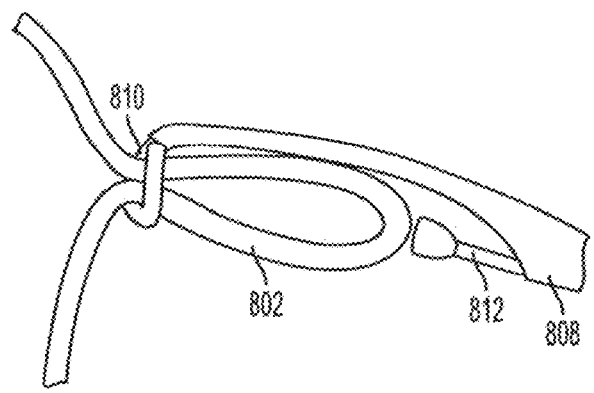

When a balloon catheter or guide element comprises a balloon and one or more electrodes and/or abrading elements proximally to the balloon, the electrodes and/or abrading elements may ablate and/or abrade, respectively, interior tissue of the left atrial appendage. For example, FIGS. 8A and 8B depict such an illustrative closure method. As shown in FIG. 8A, a balloon (800) may be advanced into the left atrial appendage (802). In some variations, the balloon (800) may be part of a balloon catheter (804) (such as the balloon catheter (700) described above with respect to FIG. 7A or the balloon catheter (710) described above with respect to FIG. 7B), and the balloon catheter (804) may be advanced along a first guide element (806), such as described above. In other variations, the balloon (800) may be part of the first guide element (such as the guide element (720) shown in FIG. 7C or the guide element (730) shown in FIG. 7D), such that advancement of the first guide element (806) into the left atrial appendage (802) also positions the balloon (800) in the left atrial appendage.

A closure device (808) may be advanced externally of the heart to position a closure assembly (810) of the closure device (808) around external tissue of the left atrial appendage (802). The closure device (808) may be advanced in any suitable manner, such as, for example, along a second guide element (812) that is positioned in the pericardial space, such as discussed in more detail above (the first and second guide elements may include magnets that may align the first and second guide elements across tissue of the left atrial appendage). Generally, the closure device (808) may be advanced to position the closure assembly past the balloon (800) (e.g., such that the closure device (808) is positioned around a portion of the balloon catheter (804) and/or first guide element (806) proximal to the balloon (800)), such as shown in FIG. 8A. As mentioned above, the balloon catheter (804) (or first guide element (806) in variations where the balloon (800) is part of the first guide element (806)) may comprise one or more elements (814), which may include one or more electrodes and/or abrading elements, such as discussed above.

With the closure device (808) and balloon (800) positioned as shown in FIG. 8A, the closure assembly (810) may be closed to place the left atrial appendage into contact with one or more of the elements (814). In variations where the one or more elements (814) comprise an electrode, the electrode may be activated to ablate the interior left atrial appendage tissue in contact with the electrodes. In variations where the one or more elements (814) comprise an abrading element, the abrading element may be moved relative to the interior left atrial appendage tissue to abrade that issue. In some variations, this may comprise rotating and/or longitudinally translating the balloon catheter (804) (or the first guide element (806) in variations where the abrading element is part of the first guide element (806)) to move the abrading element relative to the tissue to abrade the interior tissue of the left atrial appendage. In other variations, the abrading element may be moveable relative to the balloon catheter (804) and/or the first guide element (806), and may be actuated to move the abrading element relative to tissue to abrade the tissue.

Once the tissue has been abraded and/or ablated, the balloon (800), the balloon catheter (804) (in variations where the balloon (800) is part of the balloon catheter (804), and the first guide element (806) may be removed, and the closure assembly (810) may be further closed to close the left atrial appendage (802), as shown in FIG. 8B.

Figure 9A:
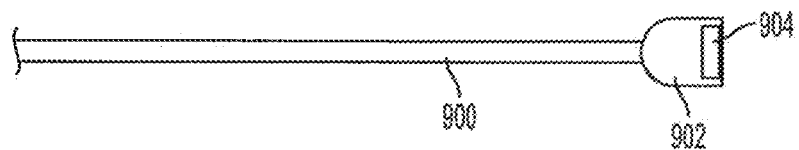
FIGS. 9A and 9B depict side views of illustrative variations of guide elements suitable for use with the systems described here.

In some variations, the distal end of a guide element may be configured to ablate interior tissue of the left atrial appendage. For example, FIG. 9A shows a variation of a guide element (900) as described here. As Shown in FIG. 9A, the guide element may comprise a magnet (902) positioned at a distal end of the guide element (900). Also shown there is an electrode (904) positioned at a distal end of the guide element (900). The electrode may be used to ablate interior tissue of the left atrial appendage, as will be described in more detail below. In some embodiments, the guide element may be configured to deliver or dispense fluid to surrounding tissue.

Figure 9B:
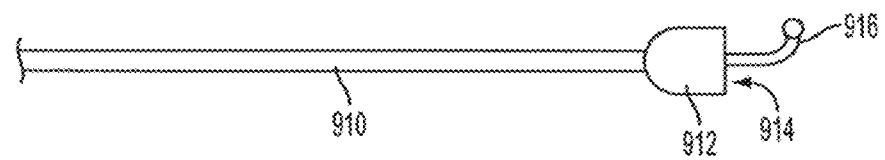

In other variations, a wire or other member may be advanced from a distal end of the guide element, and may be configured to act as an electrode to ablate tissue. For example, FIG. 9B shows another variation of a guide element (910) as described here. As shown there, the guide element (910) may comprise a magnet (912) at a distal end of the guide element (910), and may comprise a lumen (914) extending through the guide element (910). The guide element (910) may further comprise a wire (916) which may be advanced through the lumen (914) to extend from a distal end of the guide element (910). A proximal end of the wire (916) may be connected to an energy source (not shown) such that the wire (916) may act as an electrode to ablate tissue. In some variations, a proximal end of the wire (916) may be connected to a source of cryogenic fluid such that the wire (916) may be used to cryoablate tissue. In some embodiments, the wire (916) may comprise a lumen such that it may be used to dispense fluid to the surrounding tissue. The fluid may be delivered through the lumen and either out of the distal tip of the wire (916) or through side apertures along the wire's distal end. The proximal end of the wire (916) may be connected to a source of fluid, for example, a therapeutic compound or an adhesive, and the wire (916) may be used to deliver and dispense the fluid to locally affect (e.g., promote healing or closure) the surrounding tissue. The wire (916) may be any suitable wire. For example, the wire (916) may be a straight-tip or j-tip wire, may be a coiled wire, or may be configured to make another 3-dimensional shape. In some of these variations, the wire may be a ball-tipped wire.

Figure 10A:
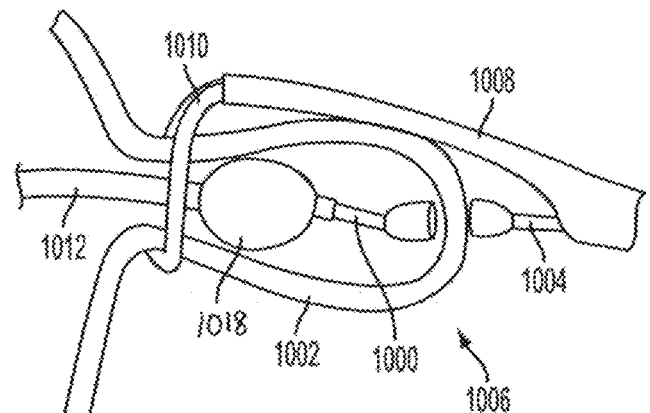
FIGS. 10A-10C depict variations of methods as described here.

When a guide element has an electrode or electrode wire at its distal end (such as the guide elements (900) and (910) described above with respect to FIGS. 9A and 9B, respectively), the guide element may be used to ablate interior tissue of the left atrial appendage. For example, FIGS. 10A, 10C shows two such variations of a method of closing a left atrial appendage. As shown in FIG. 10A, a first guide element (1000) may be positioned inside the left atrial appendage (1002) and a second guide element (1004) may be positioned externally of the left atrial appendage (1002) in the pericardial space (1006). In some variations, the first guide element (1000) and the second guide element (1004) may be aligned using magnets on each of the guide elements, such as discussed in more detail above. A closure device (1008) may be advanced over the second guide element (1004) to position a closure assembly (1010) around exterior tissue of the left atrial appendage (1002). In some variations, a balloon (1018) may be positioned in the left atrial appendage (1002) (either as part of a balloon catheter (1012) or the first guide element (1000)), such as discussed in more detail below.

With the closure assembly (1010) of the closure device (1008) encircling the left atrial appendage (1002), the first guide element (1000) (and the balloon catheter (1012) in variations where a balloon catheter (1012) is at least partially advanced into the left atrial appendage (1002)) may be removed from the interior of the left atrial appendage (1002) and the closure assembly (1010) may be closed to close the left atrial appendage. After the left atrial appendage (1002) is closed, the first guide element (1000) may be re-advanced to ablate, join or bond, or deliver drugs to the closed left atrial appendage tissue.

Figure 10B:
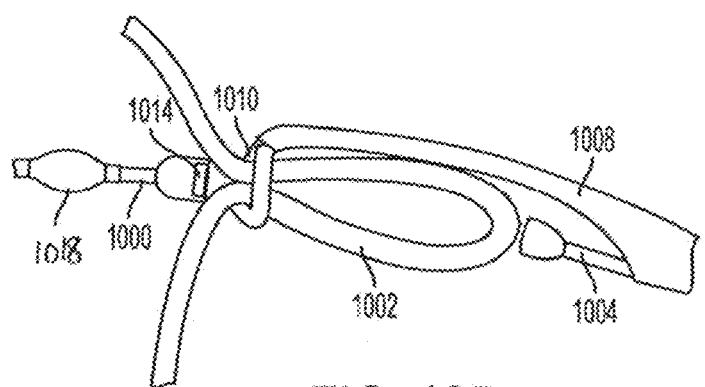
Figure 10C:
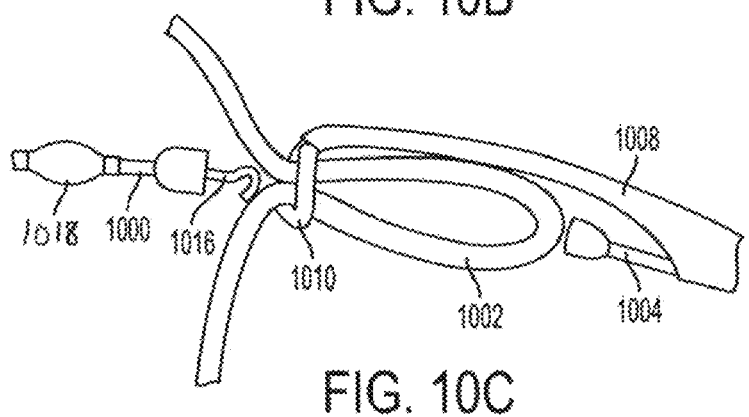

For example, in variations where the first guide element (1000) comprises an electrode (1014) at a distal end of the first guide element (1000), the first guide element (1000) may be re-advanced to place the electrode (1014) into contact with the interior tissue of the left atrial appendage (1002), as shown in FIG. 10B. Generally, this may place the electrode (1014) into contact with tissue around the ostium of the left atrial appendage (1000). The electrode (1014) may deliver RF energy to the tissue of the left atrial appendage (1002) to ablate the tissue. In some variations, the first guide element (1000) may be used with cryogenic fluid to cryoablate tissue. In some embodiments, the closure device (1008) may comprise a magnetic tip (e.g., tip (110) depicted in FIG. 1) or a magnet on its distal end to assist in guiding the distal end of the first guide element (1000) into contact with the interior tissue of the left atrial appendage (1002) in embodiments in which the first guide element (1000) comprises a magnet, as described above.

In variations where the first guide element (1000) is configured to advance a wire (1016) out of a distal end of the first guide element (1000), the wire (1016) may be advanced from a distal end of the first guide element (1000) to expose a portion of the wire (1016), and the wire (1016) may be positioned in contact with the tissue around the ostium of the left atrial appendage (1002), such as shown in FIG. 10C. In some instances this may comprise advancing the first guide element (1000) and the wire (1016) together. With the wire (1016) in contact with left atrial appendage tissue, the wire (1016) may be activated as an electrode to ablate the tissue, may be used with cryogenic fluid to cryoablate the tissue, or may be configured to locally deliver fluid, as described above.

It should be appreciated that the methods described above with respect to FIGS. 10A-10C may be used with any of the methods described above with respect to FIGS. 6A-6C and 8A-8B. In these variations, interior tissue of the left atrial appendage may be ablated or abraded, and may be closed to press the ablated/abraded tissue into contact with itself (which may assist in electrical isolation and/or invoking a healing response). The closed ostium of the left atrial appendage may then be ablated or abraded to further promote electrical isolation of the left atrial appendage and/or a healing response.

Figure 11C:
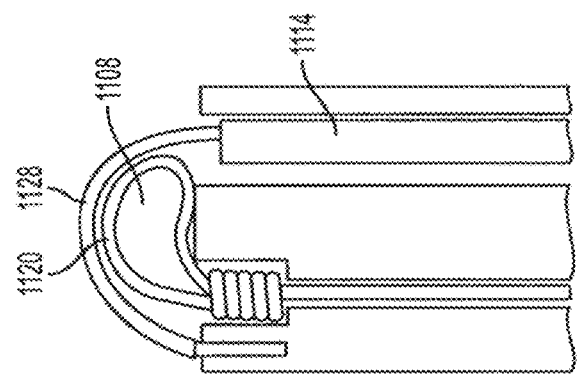
FIGS. 11A-11C, 12A-12C, and 13A-13C depict cross-sectional side views of three variations of closure devices as described here.
Figure 11B:
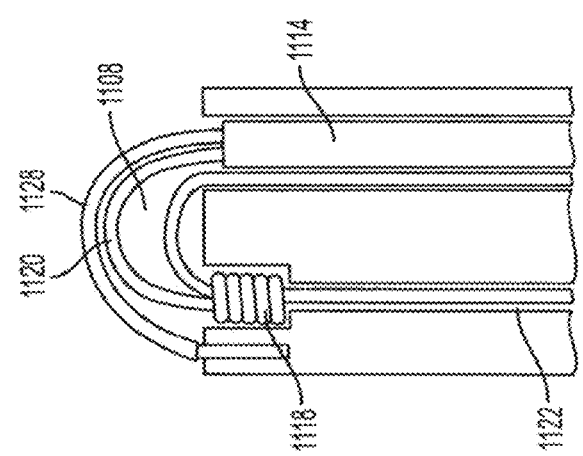
Figure 11A:
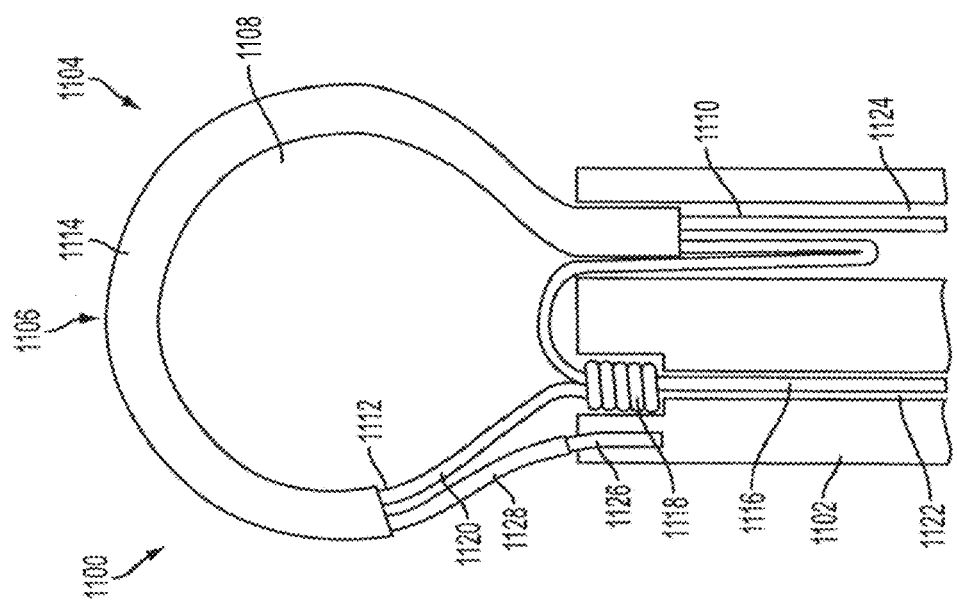

In addition to or as an alternative to ablating or abrading the interior tissue of the left atrial appendage, the closure devices described here may be configured to ablate exterior tissue of the left atrial appendage. FIGS. 11A-11C show cross-sectional side views of a distal portion of one such variation of a closure device (1100). As shown there, the closure device (1100) may comprise an elongate body (1102) and a snare loop assembly (1104), which may define a loop (1106) encircling an aperture (1108). The snare loop assembly (1104) may comprise a snare (1110), a suture loop (1112), and retention member (1114), such as discussed in more detail above. The suture loop (1112) may include a tail portion (1116), a suture knot (1118), and a loop portion (1120), such that one end of the snare (1110) extends through a first lumen (1124) in the elongate body (1102) and the tail portion (1116) of the suture loop (1112) extends through a second lumen (1122) in the elongate body. A second end (1126) of the snare (1110) may be fixed relative to the elongate body (1102). As discussed in more detail above, movement of the snare (1110) into and out of the first lumen (1124) may increase and decrease the size of the loop (1106) defined by the snare loop assembly (1104).

Also shown in FIGS. 11A-11C is an electrode (1128). The electrode (1128) may be positioned around a portion of the snare loop assembly (1006). In the variation shown in FIGS. 11A-11C, the electrode (1128) may be positioned on the snare (1110) between the fixed end (1126) of the snare (1110) and the retention member (1114), but not around the suture loop (1112). In some variations, a portion of the snare (1110) may act as an electrode (1128). Specifically, the snare (1110) may be formed from an electrically conductive material which may convey current from a proximal portion of the snare to the electrode (1128). The snare (1110) may be at least partially covered with an insulating material (such as PTFE), such that the insulating material insulates portions of the snare (1110) to prevent inadvertent ablation by the snare. The electrode (1128) may not include the insulating material to expose the conductive material of the snare (1110), which may thereby act as an electrode. It should be appreciated that the snare may also be used with cryogenic fluid (e.g., within a lumen of the snare) such that the snare may cryoablate the tissue. The snare may also comprise porous materials or apertures such that the snare may be used to dispense therapeutic compounds, adhesive, or any other desired material to the tissue. Moreover, in some variations, the electrode (1128) may comprise magnetic material or may be an electromagnet. In these variations, when the snare (1110) is closed around the external surface of the left atrial appendage, the magnetic material of electrode (1128) may externally encircle the left atrial appendage which may assist in guiding a tool (e.g., an ablation or abrading device) within the left atrial appendage or the left atrium to the closure site.

Figure 12C:
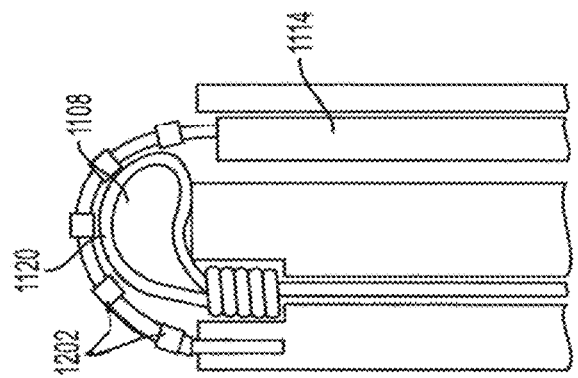
Figure 12B:
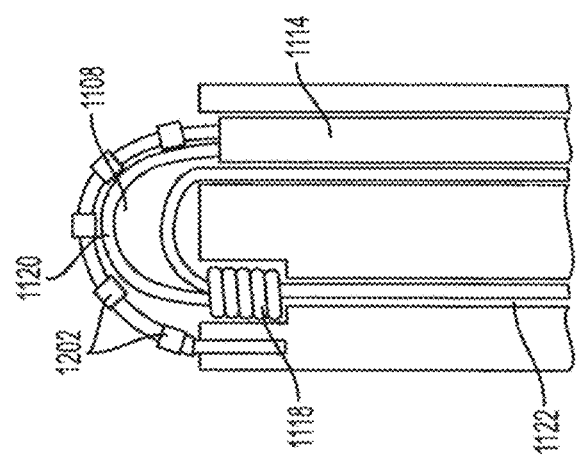
Figure 12A:
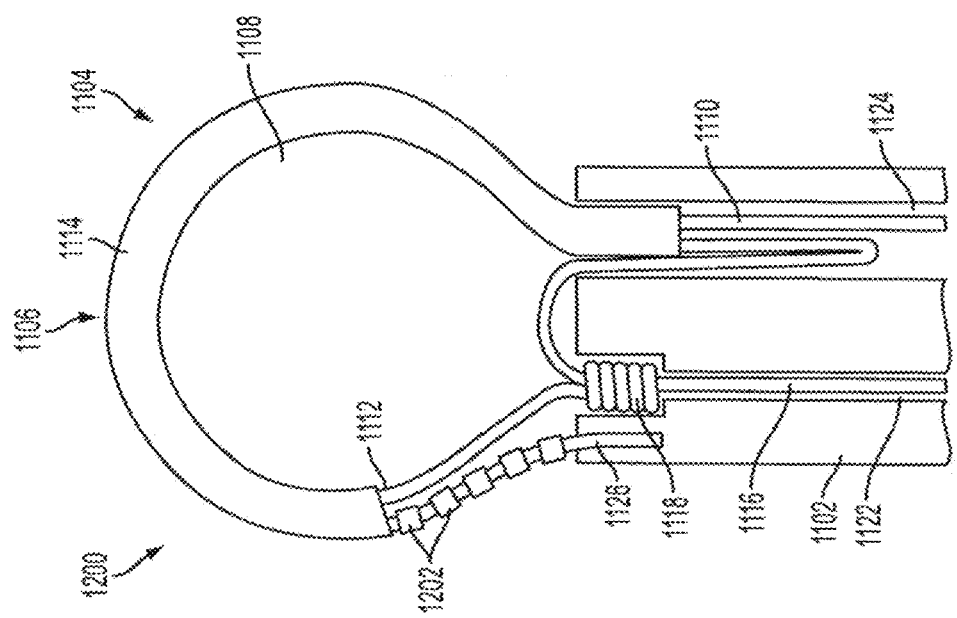

While shown in FIGS. 11A-11C as having a single electrode (1128), the closure device 1100) may comprise any suitable number of electrodes (e.g., one, two, three, or four or more electrodes). For example, FIGS. 12A-12C show another variation of a closure device (1200) having a plurality of electrodes (1202). The closure device (1200) may comprise a snare loop assembly (1104) and an elongate body (1102) as discussed above with respect to FIGS. 11A-11C (identical components are labeled as shown in FIGS. 11A-11C). As shown in FIGS. 12A-12C, the closure device may include a plurality of electrodes (1202) positioned on the snare (1110) between the fixed end (1126) of the snare (1110) and the retention member (1114). While shown in FIGS. 12A-12C as having five electrodes (1202), the snare (1110) may include any suitable number of electrodes as discussed above. In variations where the snare (1110) includes multiple electrodes (1202), some electrodes may be used to ablate tissue, while other electrodes may be used to monitor one or more aspects of tissue (e.g., one or more electrical signals, temperature, or the like).

Additionally, as described above with respect to electrode (1128), electrodes (1202) may comprise magnetic material or electromagnets. Moreover, in some variations, one or more of the elements (1202) may be replaced by magnets. In variations in which the elements (1202) comprise both electrodes and magnets, the electrodes and magnets may be arranged along the snare in any suitable configuration, for example, alternating every other element, in pairs, in groups, etc. The magnets may assist a user in locating the desired area inside of the heart as the magnets on the snare may help align a tool inside of the heart with the closure location. Additionally, in embodiments in which the elements (1202) comprise both magnets and electrodes, a user may ablate an external surface of the left atrial appendage with the electrodes and utilize the magnets to align an internal tool (ablating, abrading, or other tissue affecting device) with the external electrodes to ablate or otherwise affect the tissue at substantially the same location.

The closure devices (1100) and (1200) shown in FIGS. 11A-11C and 12A-12C respectively, may be used to ablate tissue of the left atrial appendage. For example, the snare loop assembly (1104) may be placed in an open configuration, as shown in FIGS. 11A and 12A, and may be advanced into the pericardial space to position the left atrial appendage (not shown) in the aperture (1108) of the snare loop assembly. The snare loop assembly (1104) may be closed around the left atrial appendage to close the left atrial appendage, as shown in FIGS. 11B and 12B. This may position the electrode (1128) (in the instance of the closure device (1100)) or one or more of the electrodes (1202) (in the instance of the closure device (1200)) in contact with exterior tissue of the left atrial appendage. In some instances, the exterior tissue of the left atrial appendage may be ablated at this point.

In some variations, the suture loop (1112) may be tightened to release the suture loop from the retention member (1114) and the snare loop assembly (1104), such as shown in FIGS. 11C and 12C. In some variations, the exterior tissue of the left atrial appendage may be ablated using the electrode (1128) or one or more of the electrodes (1202) after the suture loop (1112) has been released from the snare loop assembly (1104). This may be done in addition to or instead of ablation prior to the release of the suture loop (1112). In some variations, the snare loop assembly (1104) may be reclosed around the left atrial appendage prior to ablation to tighten the snare loop assembly (1104) against tissue. In some variations, the snare loop assembly (1104)

may be re-opened, repositioned, and reclosed around the left atrial appendage prior to ablation.

Figure 13C:
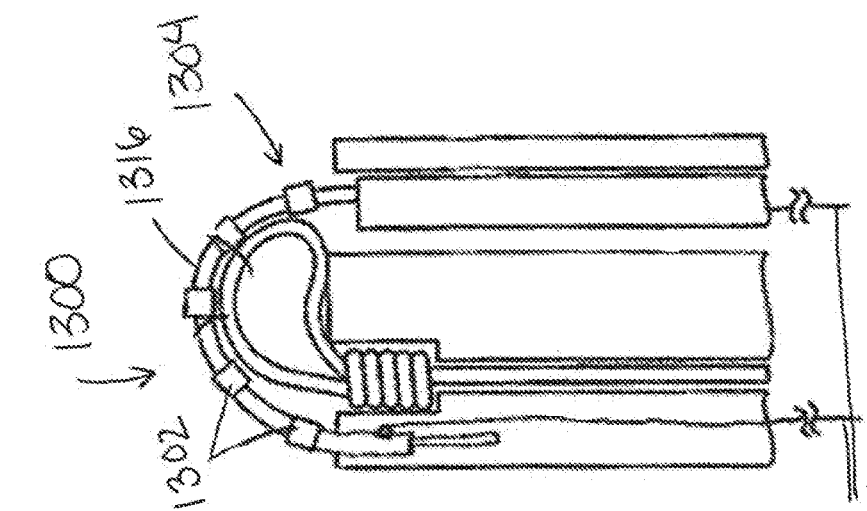
Figure 13B:
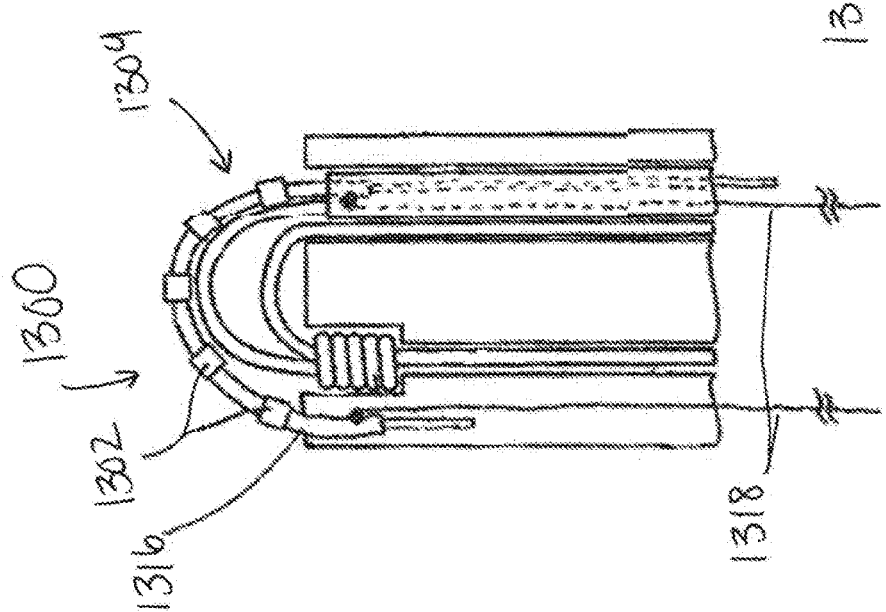
Figure 13A:
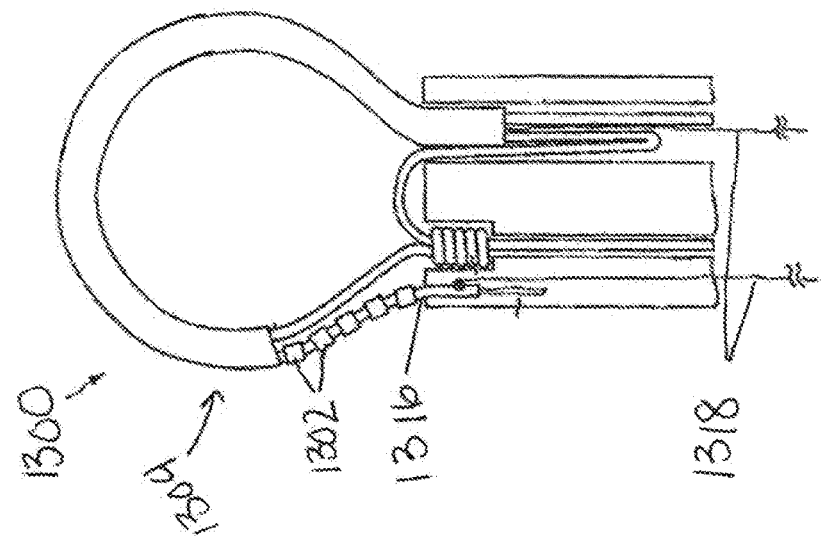

The closure device (1300) depicted in FIGS. 13A-13C may be used to abrade tissue of the left atrial appendage. As shown there, the closure device (1300) comprises a snare loop assembly (1304) similar to that described with respect to FIGS. 11A-11C and 12A-12C above, except that the snare loop assembly (1304) comprises a plurality of abrading elements (1302) instead of, or in addition to, a plurality of electrodes. The abrading elements (1302) may be disposed on an abrading member (1316) (e.g., tubing) that is slideably disposed on the snare. The abrading member (1316) may be coupled to an actuator (not depicted) on the handle or control element of the closure device (1300) through control wires (1318). A user may actuate the abrading member (1316) by alternatingly pulling the control wires (1318) such that the abrading member (1316) slides along the snare (1310). The abrading elements (1302) fixed to the abrading member (1316) are thus moved in a reciprocating motion and may be used to abrade tissue. It should be appreciated that the abrading elements (1302) may also comprise one or more electrodes to ablate tissue.

We claim:

1. A closure device for closing an atrial appendage comprising:
    an elongate body comprising a lumen therethrough;
    a snare loop assembly comprising a snare, a suture loop, and a retention member releasably coupling the snare and the suture loop, wherein the snare comprises an electrode positioned circumferentially around the snare such that the snare is concentrically within the electrode; and
    a handle configured to actuate the snare loop assembly.

2. The closure device of claim 1, wherein the snare comprises a plurality of electrodes positioned between the fixed end of the snare and the retention member.

3. The closure device of claim 2, wherein at least one electrode of the plurality of electrodes is configured to monitor a tissue parameter.

4. The closure device of claim 2, wherein a first electrode of the plurality of electrodes is configured to ablate atrial appendage tissue and wherein a second electrode of the plurality of electrodes is configured to monitor at least one tissue parameter during ablation of the tissue.

5. The closure device of claim 4, wherein the at least one tissue parameter comprises electrical signals and/or temperature.

6. The closure device of claim 1, wherein the electrode is formed from a portion of the snare that is electrically conductive.

7. The closure device of claim 6, wherein the snare is at least partially covered with an insulating material to prevent inadvertent ablation.

8. The closure device of claim 1, wherein the snare further comprises a magnet.

9. The closure device of claim 1, wherein the electrode comprises a magnetic material or is an electromagnet.

10. The closure device of claim 1, wherein the electrode is configured to assist in guiding a tool.

11. A system for closing an atrial appendage comprising:
    a closure device comprising an elongate body comprising a lumen therethrough, a snare loop assembly comprising a snare, a suture loop, and a retention member releasably coupling the snare and the suture loop, and a handle configured to actuate the snare loop assembly, wherein the snare comprises an electrode positioned circumferentially around the snare such that the snare is concentrically within the electrode;
    a first guide configured to be advanced into an interior of the atrial appendage, wherein the first guide comprises an ablating and/or abrading element, and wherein the ablating and/or abrading element is configured to ablate and/or abrade the interior of the atrial appendage; and
    a second guide configured to be advanced into a pericardial space.

12. The system of claim 11, wherein the first guide comprises a shaft and an expandable member, and wherein the shaft comprises the ablating and/or abrading element positioned proximally of the expandable member.

13. The system of claim 11, wherein the first guide comprises an expandable member, and wherein the expandable member comprises the ablating and/or abrading element.

14. The system of claim 11, further comprising at least two electrodes, wherein at least one electrode is configured to monitor at least one tissue parameter during ablation of the interior tissue.

15. The system of claim 14, wherein the at least one tissue parameter comprises temperature, ECG signals, and/or the absence of ECG signals.

16. The system of claim 14, wherein a first electrode of the at least two electrodes is configured to ablate atrial appendage tissue and wherein a second electrode of the at least two electrodes is configured to monitor at least one tissue parameter during ablation of the tissue.

17. The system of claim 11, further comprising an electrode positioned at a distal end of the first guide.

18. The system of claim 11, wherein the second guide is slideably disposed within the lumen of the elongate body to advance the closure device into the pericardial space.

19. A system for closing an atrial appendage comprising:
    a closure device comprising an elongate body comprising a lumen therethrough, a snare loop assembly comprising a snare, a suture loop, and a retention member releasably coupling the snare and the suture loop, and a handle configured to actuate the snare loop assembly, wherein the snare comprises an electrode positioned circumferentially around the snare such that the snare is concentrically within the electrode;
    a first guide configured to be advanced into an interior of the atrial appendage and comprising a lumen therethrough;
    a second guide configured to be advanced into a pericardia space and slideably disposed within the lumen of the closure device; and
    an ablating or abrading element configured to be slideably disposed within the lumen of the first guide and advanced from a distal end thereof, wherein the ablating or abrading element is configured to ablate or abrade interior tissue of the atrial appendage.

20. The system of claim 19, wherein at least one electrode is formed from a portion of the snare that is electrically conductive, wherein the snare is at least partially covered with an insulating material to prevent inadvertent ablation.

* * * * *